United States Patent
Hekmat et al.

(10) Patent No.: US 7,771,401 B2
(45) Date of Patent: Aug. 10, 2010

(54) SELECTIVE RENAL CANNULATION AND INFUSION SYSTEMS AND METHODS

(75) Inventors: Neema Hekmat, Mountain View, CA (US); Harry B. Goodson, Fremont, CA (US); Aurelio Valencia, East Palo Alto, CA (US); Jeffrey M. Elkins, Novato, CA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

(21) Appl. No.: 11/758,417

(22) Filed: Jun. 5, 2007

(65) Prior Publication Data

US 2007/0287967 A1      Dec. 13, 2007

Related U.S. Application Data

(60) Provisional application No. 60/804,261, filed on Jun. 8, 2006.

(51) Int. Cl.
*A61M 5/00*      (2006.01)

(52) U.S. Cl. .................. 604/246; 604/537; 604/284

(58) Field of Classification Search ............... 604/43, 604/95.04, 158, 246–247, 530–532, 537, 604/104–107, 284
See application file for complete search history.

(56) References Cited

U.S. PATENT DOCUMENTS

| | | | |
|---|---|---|---|
| 1,696,018 A | | 12/1928 | Schellberg |
| 2,499,045 A | | 2/1950 | Walker et al. |
| 3,144,868 A | * | 8/1964 | Jascalevich ............ 604/43 |
| 3,455,298 A | | 7/1969 | Anstadt |
| 3,516,408 A | | 6/1970 | Montanti |
| 3,667,069 A | | 6/1972 | Blackshear et al. |
| 3,730,186 A | | 5/1973 | Edmunds, Jr. et al. |
| 3,791,374 A | | 2/1974 | Guarino |
| 3,841,331 A | | 10/1974 | Wilder et al. |
| 3,995,623 A | | 12/1976 | Blake et al. |
| 4,248,224 A | | 2/1981 | Jones |
| 4,309,994 A | | 1/1982 | Grunwald |
| 4,345,602 A | | 8/1982 | Yoshimura et al. |

(Continued)

FOREIGN PATENT DOCUMENTS

DE          4324637 A1      7/1993

(Continued)

OTHER PUBLICATIONS

"Chronic Renal Insufficieny," downloaded from Internet website http://www.nutropin.com/patient/5_1_renal_insifficiency.jsp, retrieved on Nov. 13, 2006.

(Continued)

*Primary Examiner*—Nicholas D Lucchesi
*Assistant Examiner*—Theodore J Stigell
(74) *Attorney, Agent, or Firm*—Yvonne M. Horton

(57) ABSTRACT

Renal infusion systems include an infusion catheter having a bifurcated distal end with a first branch and second branch, the branches being biased to deploy laterally when unconstrained. Systems also include a delivery sheath having a lumen which receives the infusion catheter and constrains the first branch and second branch. A distal opening of the delivery sheath is formed asymmetrically to allow one of the first and second branches to open laterally while the other of the branches remains constrained. Methods of using renal infusion systems are also provided.

25 Claims, 14 Drawing Sheets

U.S. PATENT DOCUMENTS

| | | | |
|---|---|---|---|
| 4,407,271 A | 10/1983 | Schiff | |
| 4,423,725 A | 1/1984 | Baran et al. | |
| 4,459,977 A | 7/1984 | Pizon et al. | |
| 4,490,374 A | 12/1984 | Bandurco et al. | |
| 4,493,697 A | 1/1985 | Krause et al. | |
| 4,536,893 A | 8/1985 | Parravicini | |
| 4,546,759 A | 10/1985 | Solar | |
| 4,554,284 A | 11/1985 | Stringer et al. | |
| 4,636,195 A * | 1/1987 | Wolinsky | 604/509 |
| 4,685,446 A | 8/1987 | Choy | |
| 4,705,502 A | 11/1987 | Patel | |
| 4,705,507 A | 11/1987 | Boyles | |
| 4,712,551 A | 12/1987 | Rayhanabad | |
| 4,714,460 A | 12/1987 | Calderon | |
| 4,723,939 A | 2/1988 | Anaise | |
| 4,753,221 A | 6/1988 | Kensey et al. | |
| 4,781,716 A | 11/1988 | Richelsoph | |
| 4,817,586 A | 4/1989 | Wampler | |
| 4,834,707 A | 5/1989 | Evans | |
| 4,840,172 A | 6/1989 | Augustine et al. | |
| 4,846,831 A | 7/1989 | Skillin | |
| 4,861,330 A | 8/1989 | Voss | |
| 4,863,461 A | 9/1989 | Jarvik | |
| 4,888,011 A | 12/1989 | Kung et al. | |
| 4,902,272 A | 2/1990 | Milder et al. | |
| 4,902,291 A | 2/1990 | Kolff | |
| 4,906,229 A | 3/1990 | Wampler | |
| 4,909,252 A | 3/1990 | Goldberger | |
| 4,911,163 A | 3/1990 | Fina | |
| 4,919,647 A | 4/1990 | Nash | |
| 4,925,377 A | 5/1990 | Inacio et al. | |
| 4,925,443 A | 5/1990 | Heilman et al. | |
| 4,927,407 A | 5/1990 | Dorman | |
| 4,927,412 A | 5/1990 | Menasche | |
| 4,938,766 A | 7/1990 | Jarvik | |
| 4,950,226 A | 8/1990 | Barron | |
| 4,957,477 A | 9/1990 | Lundback | |
| 4,964,864 A | 10/1990 | Summers et al. | |
| 4,976,691 A | 12/1990 | Sahota | |
| 4,976,692 A | 12/1990 | Atad | |
| 4,990,139 A | 2/1991 | Jang | |
| 4,995,864 A | 2/1991 | Bartholomew et al. | |
| 5,002,531 A | 3/1991 | Bonzel | |
| 5,002,532 A | 3/1991 | Gaiser et al. | |
| 5,044,369 A * | 9/1991 | Sahota | 600/435 |
| 5,053,023 A | 10/1991 | Martin | |
| 5,059,178 A | 10/1991 | Ya | |
| 5,067,960 A | 11/1991 | Grandjean | |
| 5,069,662 A | 12/1991 | Bodden | |
| 5,069,680 A | 12/1991 | Grandjean | |
| 5,073,094 A | 12/1991 | Dorman et al. | |
| 5,087,244 A | 2/1992 | Wolinsky | |
| 5,089,019 A | 2/1992 | Grandjean | |
| 5,098,370 A | 3/1992 | Rahat et al. | |
| 5,098,442 A | 3/1992 | Grandjean | |
| 5,109,830 A | 5/1992 | Cho | |
| 5,112,301 A | 5/1992 | Fenton, Jr. et al. | |
| 5,112,349 A | 5/1992 | Summers et al. | |
| 5,119,804 A | 6/1992 | Anstadt | |
| 5,129,883 A | 7/1992 | Black | |
| 5,131,905 A | 7/1992 | Grooters | |
| 5,135,474 A | 8/1992 | Swan et al. | |
| 5,158,540 A | 10/1992 | Wijay et al. | |
| 5,160,323 A * | 11/1992 | Andrew | 604/158 |
| 5,163,910 A | 11/1992 | Schwartz et al. | |
| 5,167,628 A | 12/1992 | Boyles | |
| 5,180,364 A | 1/1993 | Ginsburg | |
| 5,205,810 A | 4/1993 | Guiraudon et al. | |
| 5,226,888 A | 7/1993 | Arney | |
| 5,256,141 A | 10/1993 | Gencheff et al. | |
| 5,257,974 A | 11/1993 | Cox | |
| 5,282,784 A | 2/1994 | Willard | |
| 5,290,227 A | 3/1994 | Pasque | |
| 5,292,309 A | 3/1994 | Van Tassel et al. | |
| 5,308,319 A | 5/1994 | Ide et al. | |
| 5,308,320 A | 5/1994 | Safar et al. | |
| 5,312,343 A | 5/1994 | Krog et al. | |
| 5,320,604 A | 6/1994 | Walker et al. | |
| 5,326,374 A | 7/1994 | Ilbawi et al. | |
| 5,328,470 A | 7/1994 | Nabel et al. | |
| 5,332,403 A | 7/1994 | Kolff | |
| 5,345,927 A | 9/1994 | Bonutti | |
| 5,358,519 A | 10/1994 | Grandjean | |
| 5,364,337 A | 11/1994 | Guiraudon et al. | |
| 5,370,617 A | 12/1994 | Sahota | |
| 5,383,840 A | 1/1995 | Heilman et al. | |
| 5,397,307 A | 3/1995 | Goodin | |
| 5,411,479 A | 5/1995 | Bodden | |
| 5,421,826 A | 6/1995 | Crocker et al. | |
| 5,429,584 A | 7/1995 | Chiu | |
| 5,453,084 A | 9/1995 | Moses | |
| 5,464,449 A | 11/1995 | Ryan et al. | |
| 5,476,453 A | 12/1995 | Mehta | |
| 5,478,331 A | 12/1995 | Heflin et al. | |
| 5,484,385 A | 1/1996 | Rishton | |
| 5,505,701 A | 4/1996 | Anaya Fernandez de Lomana | |
| 5,509,428 A | 4/1996 | Dunlop | |
| 5,536,250 A | 7/1996 | Klein et al. | |
| 5,558,617 A | 9/1996 | Heilman et al. | |
| 5,569,296 A | 10/1996 | Marin et al. | |
| 5,599,306 A | 2/1997 | Klein et al. | |
| 5,609,628 A | 3/1997 | Keranen | |
| 5,613,949 A | 3/1997 | Miraki | |
| 5,613,980 A | 3/1997 | Chauhan | |
| 5,617,878 A | 4/1997 | Taheri | |
| 5,643,171 A | 7/1997 | Bradshaw et al. | |
| 5,643,215 A | 7/1997 | Fuhrman et al. | |
| 5,669,924 A | 9/1997 | Shaknovich | |
| 5,702,343 A | 12/1997 | Alferness | |
| 5,713,853 A * | 2/1998 | Clark et al. | 604/509 |
| 5,713,860 A | 2/1998 | Kaplan et al. | |
| 5,720,735 A | 2/1998 | Dorros | |
| 5,755,779 A | 5/1998 | Horiguchi | |
| 5,762,599 A | 6/1998 | Sohn | |
| 5,766,151 A | 6/1998 | Valley et al. | |
| 5,776,190 A | 7/1998 | Jarvik | |
| 5,797,876 A | 8/1998 | Spears et al. | |
| 5,807,311 A | 9/1998 | Palestrant | |
| 5,807,895 A | 9/1998 | Stratton et al. | |
| 5,817,046 A | 10/1998 | Glickman | |
| 5,902,229 A | 5/1999 | Tsitlik et al. | |
| 5,902,336 A | 5/1999 | Mishkin | |
| 5,913,852 A | 6/1999 | Magram | |
| 5,928,132 A | 7/1999 | Leschinsky | |
| 5,935,924 A | 8/1999 | Bunting et al. | |
| 5,968,013 A | 10/1999 | Smith et al. | |
| 5,971,910 A | 10/1999 | Tsitlik et al. | |
| 5,984,955 A | 11/1999 | Wisselink | |
| 6,001,079 A | 12/1999 | Pourchez | |
| 6,013,054 A | 1/2000 | Jiun Yan | |
| 6,039,721 A | 3/2000 | Johnson et al. | |
| 6,068,629 A | 5/2000 | Haissaguerre et al. | |
| 6,077,256 A | 6/2000 | Mann | |
| 6,086,527 A | 7/2000 | Talpade | |
| 6,086,557 A | 7/2000 | Morejohn et al. | |
| 6,096,073 A | 8/2000 | Webster et al. | |
| 6,117,117 A | 9/2000 | Mauch | |
| 6,117,156 A | 9/2000 | Richter et al. | |
| 6,142,973 A | 11/2000 | Carleton et al. | |
| 6,143,002 A | 11/2000 | Vietmeier | |
| 6,156,016 A | 12/2000 | Maginot | |
| 6,165,120 A | 12/2000 | Schweich, Jr. et al. | |
| 6,190,349 B1 | 2/2001 | Ash et al. | |
| 6,210,380 B1 | 4/2001 | Mauch | |

| | | | |
|---|---|---|---|
| 6,251,133 B1 | 6/2001 | Richter et al. | |
| 6,261,273 B1 | 7/2001 | Ruiz | |
| 6,261,316 B1 | 7/2001 | Shaolian et al. | |
| 6,287,277 B1 | 9/2001 | Jiun Yan | |
| 6,287,608 B1 | 9/2001 | Levin et al. | |
| 6,325,826 B1 | 12/2001 | Vardi et al. | |
| 6,387,037 B1 | 5/2002 | Bolling et al. | |
| 6,390,969 B1 | 5/2002 | Bolling et al. | |
| 6,468,241 B1 | 10/2002 | Gelfand et al. | |
| 6,475,208 B2 | 11/2002 | Mauch | |
| 6,482,211 B1 | 11/2002 | Choi | |
| 6,494,875 B1 | 12/2002 | Mauch | |
| 6,508,787 B2 | 1/2003 | Erbel et al. | |
| 6,514,226 B1 | 2/2003 | Levin et al. | |
| 6,533,747 B1 | 3/2003 | Polaschegg et al. | |
| 6,540,779 B2 | 4/2003 | Richter et al. | |
| 6,544,206 B1 | 4/2003 | Johnston, Jr. | |
| 6,592,567 B1 | 7/2003 | Levin et al. | |
| 6,595,959 B1 | 7/2003 | Stratienko | |
| 6,669,718 B2 | 12/2003 | Besselink | |
| 6,699,231 B1 | 3/2004 | Sterman et al. | |
| 6,733,474 B2 | 5/2004 | Kusleika | |
| 6,749,598 B1 | 6/2004 | Keren et al. | |
| 6,749,628 B1 | 6/2004 | Callol et al. | |
| 6,884,258 B2 | 4/2005 | Vardi et al. | |
| 6,887,258 B2 | 5/2005 | Denison et al. | |
| 6,911,039 B2 | 6/2005 | Shiu et al. | |
| 6,945,992 B2 | 9/2005 | Goodson et al. | |
| 6,994,700 B2 | 2/2006 | Elkins et al. | |
| 7,104,981 B2 | 9/2006 | Elkins et al. | |
| 7,381,204 B2 | 6/2008 | Wilson et al. | |
| 7,470,252 B2 * | 12/2008 | Mickley et al. | 604/103.02 |
| 2001/0029349 A1 | 10/2001 | Leschinsky | |
| 2001/0031907 A1 | 10/2001 | Downey et al. | |
| 2002/0022857 A1 | 2/2002 | Goldsteen et al. | |
| 2002/0090388 A1 | 7/2002 | Humes et al. | |
| 2002/0091355 A1 | 7/2002 | Hayden | |
| 2002/0165574 A1 | 11/2002 | Ressemann et al. | |
| 2002/0169413 A1 | 11/2002 | Keren et al. | |
| 2003/0050600 A1 | 3/2003 | Ressemann et al. | |
| 2003/0069468 A1 | 4/2003 | Bolling et al. | |
| 2003/0100919 A1 | 5/2003 | Hopkins et al. | |
| 2003/0144636 A1 | 7/2003 | Liu | |
| 2003/0153898 A1 | 8/2003 | Schon et al. | |
| 2003/0181856 A1 | 9/2003 | Goldman | |
| 2003/0220664 A1 | 11/2003 | Petrick et al. | |
| 2004/0002730 A1 | 1/2004 | Denison et al. | |
| 2004/0044302 A1 | 3/2004 | Bernard et al. | |
| 2004/0064089 A1 | 4/2004 | Kesten et al. | |
| 2004/0097900 A1 | 5/2004 | Keren et al. | |
| 2004/0111148 A1 | 6/2004 | Goodson | |
| 2004/0117003 A1 | 6/2004 | Ouriel et al. | |
| 2004/0167415 A1 | 8/2004 | Gelfand et al. | |
| 2004/0167463 A1 | 8/2004 | Zawacki et al. | |
| 2004/0254236 A1 | 12/2004 | Dong et al. | |
| 2005/0027305 A1 | 2/2005 | Shiu et al. | |
| 2005/0197624 A1 | 9/2005 | Goodson et al. | |
| 2005/0245882 A1 | 11/2005 | Elkins et al. | |
| 2005/0245892 A1 | 11/2005 | Elkins et al. | |
| 2005/0267010 A1 | 12/2005 | Goodson et al. | |
| 2006/0030814 A1 | 2/2006 | Valencia et al. | |
| 2006/0036218 A1 | 2/2006 | Goodson et al. | |
| 2006/0047266 A1 | 3/2006 | Elkins et al. | |
| 2006/0069323 A1 | 3/2006 | Elkins et al. | |
| 2006/0079836 A1* | 4/2006 | Holman et al. | 604/96.01 |
| 2006/0079859 A1* | 4/2006 | Elkins et al. | 604/508 |
| 2006/0149350 A1 | 7/2006 | Patel et al. | |
| 2006/0259066 A1 | 11/2006 | Euteneuer | |
| 2007/0053904 A1 | 3/2007 | Kirst et al. | |

FOREIGN PATENT DOCUMENTS

| | | | |
|---|---|---|---|
| EP | 654283 | A1 | 11/1994 |
| EP | 884064 | A2 | 5/1998 |
| GB | 2239675 | A | 7/1994 |
| WO | WO 97/11737 | | 4/1997 |
| WO | WO 98/03213 | A1 | 1/1998 |
| WO | WO 98/17347 | A1 | 4/1998 |
| WO | WO 98/52639 | A1 | 11/1998 |
| WO | WO 99/33407 | A1 | 12/1998 |
| WO | WO 99/22784 | A1 | 5/1999 |
| WO | WO 99/51286 | A1 | 10/1999 |
| WO | WO 00/41612 | A2 | 1/2000 |
| WO | WO 01/83016 | | 4/2001 |
| WO | WO 01/37882 | A | 5/2001 |
| WO | WO 01/41861 | A1 | 6/2001 |
| WO | WO 01/97687 | | 12/2001 |
| WO | WO 01/97717 | | 12/2001 |
| WO | WO 01/97878 | A1 | 12/2001 |
| WO | WO 01/97879 | A1 | 12/2001 |
| WO | WO 2004/026370 | A | 4/2004 |
| WO | WO 2004/032791 | A | 4/2004 |
| WO | WO 2005/002660 | A1 | 1/2005 |
| WO | WO 2005/014100 | A1 | 2/2005 |

OTHER PUBLICATIONS

"Diabeted Mellitus," University of Maryland Medical Center webpage, retrieved from http://www.umm.edu/altmed/ConsConditions/DiabetesMellituscc.html on Nov. 13, 2006.

"FDA Form 510(K) on Related Correspondence for Advanced Equipment Development, Inc."

Agostoni et al. Sustained Benefit from Ultrafiltration in Moderate Congestive heart failure Cardiology 2001:96 183-189.

Akaba, N. et al.; "A Cylinder-Shaped Balloon Catheter for the Management of Dissecting Aneurysms in Acute Stage," Herz, vol. 17, No. 6, pp. 390-393, Dec. 1992. Abstract Only.

Aspelin, et al., "Nephrotoxic Effects in High-Risk Patients Undergoing Angiography," N Engl J Med, Feb. 2003, vol. 348, No. 6, pp. 491-499.

Bakris, et al., Renal Hemodynamics in Radiocontrast Medium-Induced Renal Dysfunction etc. Kidney Internation, vol. 56 pp. 206-210 (1999).

Beregi, et al., "Doppler Flow Wire Evaluation of Renal Blood Flow Reserve in Hyertenstive Patient With Normal Renal Arteries," Cardiovascular and Interventional Radiology, vol. 23, pp. 340-346 (2000).

Bergey, E.A. et al.; "Transhepatic Insertion of Vascular Dialysis Catheters in Children: A Safe, Life-Prolonging Procedure," Pediatr. Radiol., vol. 29, No. 1, pp. 42-50, Jan. 1999. Abstract Only.

Bischoff, W. et al.; "Modified in Suty Perfusion of the Kidney Using Balloon Catheters," vol. 94, No. 30, pp. 1695-1697, Oct. 21, 1976. Abstract Only.

Briguori et al., "Contrast Agent-Assocaited Nephrotoxicity," Progress in Cardiovascular Diseases, 45;6(2003): 493-503.

Canaud, B. et al.; "Temporary Vascular Access for Extracorporeal Renal Replacement Therapies in Acute Renal Failure Patients," Kidney Int. Suppl., vol. 66, pp. S142-S150, May 1998. Abstract Only.

Chatterjee, "Refractory heart failure-drugs and devices", European Heart Journal, 2001, 22:2227-2230.

Chu, et al. "Fenoldopam in the Prevention of Contrast Media-Induced Acute Renal Failure," The Annals of Pharmacotherapy, 35:1276-1282 (2001).

Cohn, Jay N.; "The Management of Chronic Heart Failure," The New England Journal of Medicine, pp. 490-498. Aug. 15, 1996.

Darves, "ASHP: Perioperative Fenoldopam Improves Renal Function During Major Surgery," Retrieved from the Internet [Online]: www.pslgroup.com/dg/225C72.htm, Dec. 19, 2002.

Del Greco, The Kidney in Congestive Heart Failure, Modern Concepts of Cardiovascular, Sep. 1975, vol. 44, No. 9, pp. 47-52.

D'Elia, et al., Nephrotoxicity from Angiographic Contrast Material, "A prospective Study," Am J Med, May 1982, vol. 72, pp. 719-725.

Diaz-Sandoval, et al., "Acetylcysteine to Prevent Angiography-Related Renal Tissue Injury," The American Journal of Cardiology, Feb. 1, 2002: vol. 89, pp. 356-358.

Drescher, et al., Prevention of Contrast Medium-Induced Renal Vasospasm by Phosphodiesterase Inhibition, Ivest Radiol 1998; 33:858-862.

Eisenberg, et al., Renal Failure After Major Angiography Can be Avoided with Hydration, AJR, May 1981; 136:859-861.

Eisenberg, et al., Renal Failure After Major Angiography, Am J Med, Jan. 1980, vol. 68, pp. 43-46.

Eisenberger, F. et al.; "Transfemoral Cannulation of the Renal Vessels. Diagnostic and Therapeutic use in Urology," Urologe [A], vol. 16, No. 1, pp. 1-5, Jan. 1977. Abstract Only.

Elkayam, et al., Renal Hemodynaic Effects of Vasodilation with Nifedipine and Hydralazine in Patients With Heart Failure, JACC Dec. 1984; vol. 4, No. 6, pp. 1261-1267.

Elkayam, et al., Renal Vasodilatory Effect of Endothelial Stimulation in Patients with Chronic Congestive Heart Failure, J Am Coll Cardiol 1996;28:176-182.

Encarta dictionary, "Prevent," downloaded from website http://encarta.msn.com/encnet/features/dictionary/DictionaryResults.aspx?refid=1861737040, 2007, 1 page, retrieved Apr. 18, 2007.

Farncombe, "Dyspnea: assessment and treatment," Support Care Cancer, 1997, 5, 94-99.

Fox, S.L.; "Mechanisms of Contraction," Human Physiology, Fourth Edition, pp. 300-323.

Freeman, et al., "Nephropathy Requiring Dialysis After Percutaneous Coronary Intervention and the Critical role of an Adjusted Contrast Dose," Am J Cardiol, vol. 90, (Nov. 15, 2002) pp. 1068-1073.

Garwood, Susan et al.; "Renal Preservation Strategies for High Risk Patients,"University of Chico School Medicine, Cover Page, Table of Contents Page, pp. 1-19, 1998.

Geisburg et al., "Addressing the Challenges of Cardiorenal Syndrome," Clevland Clinic Journal of Medicine, 2006, 73, 485-491.

Gerlach, et al., "Contrast Medium-Induced Nephrotoxicity: Pathophysiology and Prevention," *Pharmacotherapy*, 2000, 20(5):540-548.

Gianello et al., Clinical Transplantation, 1995, 9, 481-489.

Greco, B.A. et al.; "Atherosclerotic Ischemic Renal Disease," Am. J. Kidney Dis., vol. 29, No. 2, pp. 167-187, Feb. 1997. Abstractly Only.

Gruberg, et al. The prognostic implications of further renal deterioration within 48 h of interventional etc. J AM Coll Cardiol 2000, 20(5):540-548.

Halpenny et al. The effects of fendolopam on renal blood flow and tubular function during aortic cross-damping in anaesthetized dogs, EUR J Anaetesthesiol, Aug. 2000: 17(8); 491-8 Abstract.

Heyman, et al., Pathophysiology of Radiocontact Nephropathy, A Role for Medullary Hypoxia, Invest Radiol, 1999; 34:685-691.

Hobbs, et al., "An Update on Nesiritide for Treatment of Decompensated Heart Failure," *Exp. Opin. Invest. Drugs*, 2001, 10(5):935-942.

Houghton, et al., "Basal and Reserve Renal Artery Blood Flow: Effect of Endothelium-Dependent and Independent Vasoactive Agonists and Radiographic Contrast Medium in Two Patients", *J invas Cardiol* 2000, 12: 211-215.

Hunter et al., "Preventing Contrast-Induced Nephropathy with Fenoldopam," Techniques in Vascular and Inverventional Radiology. 2001. 4:1:53-56.

Iannone, L.D. et al.; "Effect of Primary Balloon Expandable Renal Artery Stents o Long-Term Patency, Renal Function, and Blood Pressure in Hypertensive and Renal Insufficient Patients with Renal Artery Stenosis," Cathet. Cardiovasc. Dign., vol. 37, No. 3, pp. 243-250, Mar. 1996. Abstract Only.

Jacobs, M.J. et al.; "Reduced Renal Failure Following Thoracobdominal Aortic Aneurysm Repair by Selective Prefusion," Eur. J. Cardiothorac. Surg., vol. 14, No. 2, pp. 201-205, Aug. 1998. Abstract Only.

Katsumata T. et al.' "Newly-Developed Catheter for Cardio-Renal Assist During Intraaortic Balloon Counterpulsation," Kyobu Geka, vol. 46, No. 9, pp. 767-770, Aug. 1993. Abstract Only.

Kay, et al., Acetylcysteine for Prevention of Acute Deterioration of Renal Function Following Elective Coronary Angiography and Intervention, *JAMA*, vol. 289 No. 5, (Feb. 5, 2003).

Kehrer et al.; "Construction and Experimental Application of a Catheter for Selective Arterial Kidney Perfusion in Situ," Urological Research, vol. 13, pp. 85-89, 1985.

Kim, et al., Fluriscopic Landmarks for Optimal Visualization of the Proximal Renal Arteries, JVIR, 10:37-39 (1999).

Kini et al. A protocol for Prevention of Radiographic contrast Nepropathy etc. Catheterization and Cardiovascular Interventions 2002, 55:169-173.

Kini et al. Managing the High-Risk Patient: Experience with Fenoldopam etc. Rev. Cardiovas Med 2001:2(suppl 1) S19-S25.

Kobayashi, A. et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682-684, May 25, 1992. Abstract Only.

Kou-Gi Shyu et al., "Acetylcysteine Protects Against Acute Renal Damage in Patients with Abnormal Renal Function Undergoing a Coronary Procedure," The Journal of the American College of Cardiology, 2002; 40:8.

Lass, et al., Cardiocascular and Renal Hemodynamic Effects of Intravenous Infusions of the Selective DA1 Agonist ec., Circulation 1988; 78:1310-1315.

Levin, Howard, R. et al.; "Reversal of Chronic Ventricular Dilation in Patients with End-Stage Cardiomyopathy by Prolonged Mechanical Unloading," vol. 91, No. 11, pp. 2727-2748, Jun. 1, 1995.

Linden, R.J. et al.; "The Nature of the Atrial Receptors Responsible for a Reflex Decrease in Activity in Renal Nerves of the Dog," The Physiological Society, pp. 31-40, 1980.

Madyoon, "Clinical Experience with the Use of Fenoldopam for Prevention of Radiocontrast Hephropathy etc," *Rev Cardiovasc Med*. 2001, 2(suppl 1 ); S26-S30.

Madyoon, Use of Fenoldopam to Prevent Radiocontrast Nephropathy etc. Catherization and Cardiovascular Interventions 2001, 53:341-345.

Margulies, et al., Induction and Prevention of Radiocontrast-Induced Nephropathy in Dogs with Heart Failure, Kidney Int. 1990; vol. 38:1101-1108.

Margulies, et al., Intra-Arterial Atrial Natriuetic Factor (ANF) Attenuates Radiocontrast-Induced etc., Renal Pathology, unknown date, pp. 666, Abstract only.

Masaki, Z. et al.; "In Situ Perfusion by Retrograde Cannulation of a Tumor Artery for Nephron-Sparing Surgery," Int. J. Urol, vol. 2, No. 3, pp. 161-165, Jul. 1995. Abstract Only.

Mason, et al., Renal Dysfunction After Arteriography, JAMA, 1985;253:1001-1004.

Mathis, J. M. et al.; "Use of Guide Catheter as a Temporary Stent During Microcatheter Intervention," AJNR Am. J. Neuroradiol, vol. 19, No. 5, pp. 932-933, May 1998. Abstract Only.

Mathur et al., The effects of fenoldopam, a selective dopamine receptor agonist, on renal hemodynamics etc. Abstract only. Crit Cre Med Sep. 1999: 27(9) 1832-1837.

Mathur, "The Role of the DA1 Receptor Agonist Fenoldopam in the Management of Critically Ill, Transplant, and Hypertensive Patients," *Reviews in Cardiovascular Medicine*, 2003;4(Supp 1):S35-S40.

Mccarthy, Animal Models in Medical Device Development and Qualification, Charles River Laboratories, vol. 10(2) 1997.

Mccullough, et al., Acute Renal Failure after Coronary Intervention: Incencence, Risk Factors, and Relationship to Mortality, Am J Med. 1997; 103:368-375.

Mehran, et al., "A Risk Score for Prediction of Contrast Induced nephropathy After Percutaneous Coronary Intervention," Retrieved from the Internet [Online]: www.abstractsonline.com/viewer, Mar. 31, 2003.

Mehran, et al., "Radiocontrast-Induced Acute Renal Failure: Allocations and Outcomes," *Rev Cardiovasc Med* 2001;2(suppl1):S9-S13.

Middleton, J. P.; "Ischemic Disease of the Kidney: How and Why to Consider Revascularization," J. Nephrol., vol. 11, No. 3, pp. 123-136, May-Jun. 1998. Abstract Only.

Miller, et al., "Effects of Fenoldopam on Renal Blood Flow and Tubular Function Following Suprarenal Aortic Cross-Clamping," *Ann Vasc Surg*, 2003, Published online Oct. 23, 2003. Abstract Only.

Mintz, et al., "Radiocontrast-Induced Nephropathy and Percutaneous Coronary Intervention," *Expert Opin. Pharmacother.*, 2003; 4(5):639-652.

Mueller et al. Prevention of Contrast Media Associated Nephropathy, Arch Intern Med, Feb. 2002, vol. 162 pp. 329-336.

Murray et al., "Clinical Anesthesiology: Third Edition." McGraw-Hill Professional. New York. 2002.
Nohria et al. Medical Management of Advanced Heart Failure, JAMA, Feb. 6, 2002, vol. 162, pp. 628-640.
Novick, A.C.; "Atherosclerotic Ischemic Nephropathy. Epidemiology and Clinical Considerations," Urol Clin. North Am., vol. 21, No. 2, pp. 195-200, May 1994. Abstract Only.
Paganini, et al., "Severity Scores and Outcomes With Acute Renal Failure in the ICU Setting," *Contrib Nephrol*, 2001; 132: 181-195.
Parfrey, et al., Contrast Material-Induced Renal Failure in Patients with Diabetes Mellitus, Renal Insufficiency, or Both, N Engl J Med, 1989, 320:149-153.
Patel, et al., Intravenous Fenoldopam Infusion in Severe Heart Failure, Cardiovasc Drugs Ther 1993; 7:97-101.
Pharmacy and Therapeutics Committee, Fenoldopam Mesylate (Corlopam) Usage Guidelines:, Clinical Pharmacy Associaates, Inc. Feb. 2001. http://www.clinpharm.com/client_data/productfiles/fenoldopam%20usage%20guidelines.pdf Access Nov. 29, 2007.
Pierce, "Fenoldopam (Corlopam) DUE", Pharmacy & Therapeutics Committee, Jan. 2002, http://prodruginfo.com/Formulary/DUE/fenolddue.pdf, Accessed Sep. 12, 2007.
Postma, C.T. et al.; "Treatment of Renal Artery Stenosis with Intra-Arterial Stents," Ned Tijdshr Genneeskd., vol. 142, No. 39, pp. 2132-2137, Sep. 26, 1998. Abstract Only.
Ramanathan, et al., Ameliorating Contrast-Induced Nephropathy, Journal of Invasive Cardiology, Nov. 2001, Retrieved from the Internet [Online]: www.invasivecardiology.comlfic_20011/jic_200111f6.html.
Rebeiz, et al., "Radiocontrast Nephropathy: a Time for Affirmative Action, *J Invasive Cardiology*," Jan. 2003; vol. 15, No. 1, pp. 23-24.
Rihal, et al., "Incidence and Prognostic Importance of Acute Renal Failure After Percutaneous Coronary Intervention," *Circulation*, (May 14, 2002), 105:2259-2264.
Ritchie, et al., "Use of nonionic or Low Osmolar Contrast Agents in Cardiovascular Procedures," Retrieved from the Internet [Online] www.acc.org/clinical/position/72543.htm, Jan. 22, 2003.
Robinson, et al., "Congestive Heart Failure: Targeted Drug Therapy and Invasive Interventions", Retrieved from the Internet [Online] www.speroff.com/articlesITextbook/66_CHF2.htm, printed Sep. 4, 2002.
Rudnick, et al., Nephrotoxicity of Ionic and Noionic Contrast Media in 1196 Patients: A Randomized Trial, Kidney International, 1995; 47:254-261.
Schwab, et al., Contrast Nephrotoxicity: A Randomized Controlled Trial of a Nonionic and an Ionic Radiographic Contrast Agent, N Engl J Med, 1989, 320:149-153.
Seiter, H. et al.; "Modified T-Catheter and its use for Transvenous Hypothermic in Situ Perfusion in the Surgical Restoration of the Kidney with Staghorn calculi," Z. Uro Nephrol., vol. 76, No. 6, pp. 403-406, Jun. 1983. Abstract Only.
Sheifer, "Sex Differences in Coronary Atery Size", American Heart Journal, 2000; 139(4):649-653.
Shusterman, et al., Fenoldopam, But Not Nitroprusside, Improves Renal Function etc. Am J of Medicine, 95:161-168 (1993).
U.S. Appl. No. 09/165,333—Leschinsky, Boris—"Method and Apparatus for Treating Aneurysms".
Solomon, et al., Effects of Saline, Mannitol, and Furosemide on Acute Decreases in Renal Function etc., N Engl J Med 1994; vol. 331 No. 21 pp. 1416-1420.
Stevens, et al., A Prospective Randomized Trail of Prevention Measures in Patients at High Risk for Contrast Nephropathy, J Am Coll Cardiol, 1999, 33:403-411.
Strick, et al., Direct Measurement of Renal Medullary Blood Flow in the Dog, Am J. Physiol. 267 (Regulatory Integrative Comp. Physiol. 36): R253-R2259, 1994.
Suehiro, et al., "Selective Renal Vasodilation and Active Renal Artery Perfusion Improve Renal Function in Dogs with Acute Heart Failure," *The Journal of Pharmacology and Experimental Therapeutics*, vol. 298, No. 3 pp. 1154-1160 (2001).
Taliercio, et al., Risks for Renal Dysfunction with Cardiac Angiography, Annals of Internal Medicine, 1986; 104:501-504.
Thatipelli et al., "CT Angiography of Renal Artery Anantomy for Evaluating Embolic Protection Devices." Journal of Vascular and Interventional Radiology. 2007; 18(7): 842-846.
Thomas, et al., Glomerrular Filtration Dynamics During Renal Vasodilation etc. Am. J. Physiol. 244:F606-F611 (1983).
Thomas, et al., Influence of Bradykinin and Papaverine on Renal etc., Renal Physiology, Basel 5:197-205 (1982).
Tumlin et al., "Fenoldopam Mesylate Blocks Reductions in Renal Plasma Flow After Radiocontrast Dye Infusion: A Pilot Trial in the Prevention of Contrast Nephropathy," The American Heart Journal, 2002; 143:5:894-903.
UIC College of Pharmacy, "Is Fenoldopam (Corlopam) Useful for the Prevention Of Contrast Media Associated Nephrotoxicity?", Retrieved from the Internet [Online] www.uic.edu/pharmacy/services/di/fenoldopam.htm, Jan. 2003.
Umrani et al., Beneficial effects of fenoldopam treatment on renal function in streptozotocin-induced diabetic rats, Clin Exp Hypertens, Apr. 24, 2002 (3): 207-19 Abstract only.
Van Der Zander et al., "Hypertension: Does Brain Natrriuretic Paptide Have a Direct Renal Effect in Human Hypertensives?", American Heart Association, 2003, 41, 119-123.
Vari, et al., Induction, Prevention and Mechanisms of Contrast Media-Induced Acute Renal Failure, Kidney International, 1988; 33:669-707.
Venkatamaran, "Prevention of acute renal failure," Crit. Care Clin., 2005, 21(2), 281-289 (abstract).
Walker, H.S. et al.; "Use of a Balloon-Tipped Profusion Catheter for Renal Preservation During Suprarenal Abdominal Aortic Operations," J. Vasc. Surg., vol. 2, No. 2, pp. 337-339, Mar. 1985. Abstract Only.
Weisberg et al., Risk of radiocontrast nephropathy in patients with and without diabetes mellutus, Kidney International, 1994, 45:259-265.
White, C.J. et al.; "Renal Artery Stent Placement: Utility in Lesions Difficult to Treat with Balloon Angioplasty," Am. Coll. Cardiol., vol . 30, No. 6, pp. 1445-1450, Nov. 15, 1997. Abstract Only.
Williams, D.M. et al.; "Design and Testing of a High-FLo2 Autoperfusion Catheter: An Experimental Study," J. Vasc. Interv. Radiol., vol. 3, No. 2, pp. 285-290, May, 1992. Abstract Only.
Zacherl, et al. Periarterial Papverine Applications Improves Intraoperative Kidney Function etc. Journal of Surgical Research 103:268-271 (2002).
Madyoon et al., "Fenoldopam for prevention of contrast-induced renal dysfunction in a high risk angiography population: A historically-controlled case series", Circulation vol. 104, No. Suppl. 17, XP009098219, Oct. 23, 2001, p. II-185.
Mathur, V.S., "Pathophysiology of radiocontrast nephropathy and use of fendopolam for its prevention", Reviews in Cardiovascular Medicine, vol. 2, No. Suppl. 1, 2001, pp. 54-58, XP009098238.
Stone, G.W. et al., "Designand rationale of Contrast—a prospective, randomized, placebo-controlled trial of fenoldopam mesylate for the prevention of radiocontrast nephropathy", Reviews in Cardiovascular Medicine, vol. 2, No. Suppl.1, 2001, pp. 531-536, XP009098217.
Tumlin et al., "A multicenter, double-blind, placebo-controlled trial of fenoldopam meysylate in the prevention of radiocontrast nephropathy in patients with moderate to severe renal insufficiency" Journal of the American Society of Nephrology, Vo. 11, Sep. 2000, p. 135A, XP009098223.
Tumlin, J.A. et al., Fenoldopam mesylate blocks reductions in renal plasma flow after radiocontrast dye infustion: a pilot trial in the prevention of contrast nephropathy:, Americal Heart Jourornal, vol. 143, No. 5, May 2002, pp. 894-903, XP002475379.

* cited by examiner

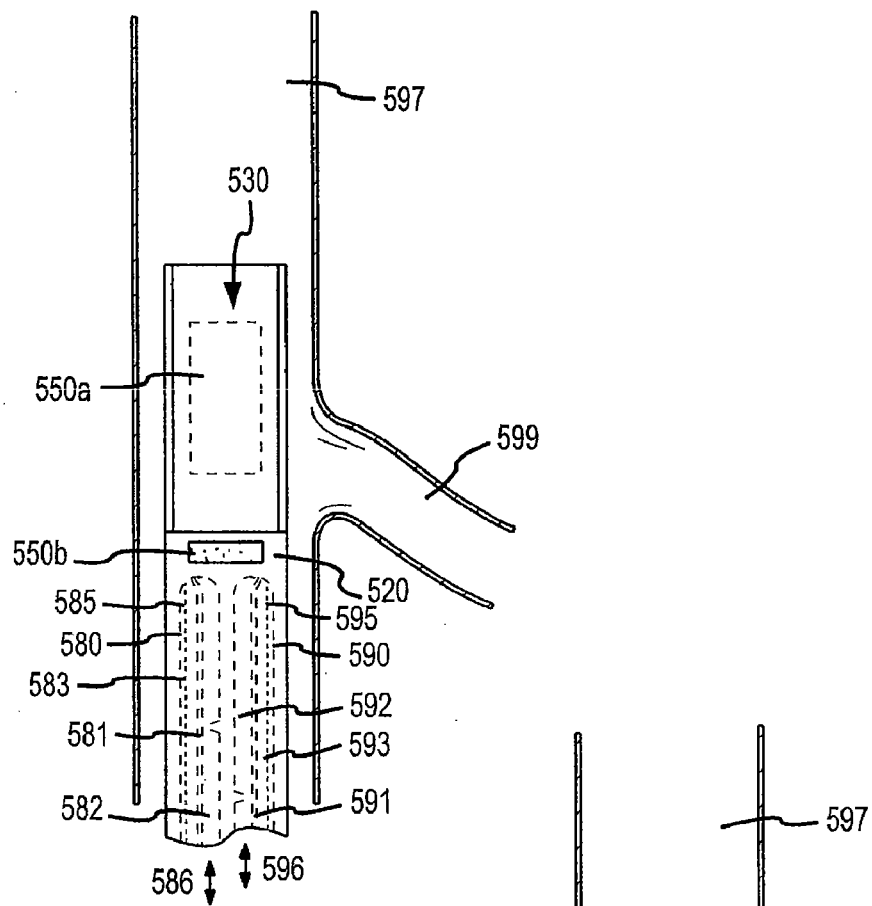
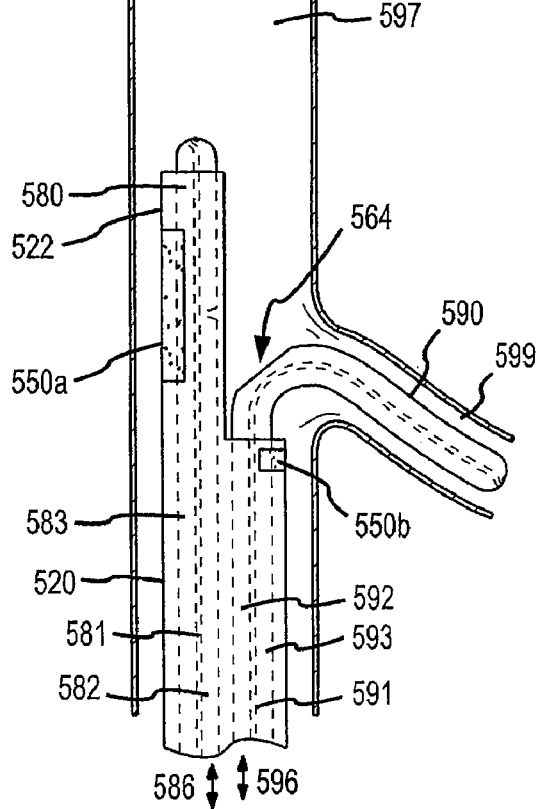
FIG.5A
FIG.5B

SELECTIVE RENAL CANNULATION AND INFUSION SYSTEMS AND METHODS

CROSS-REFERENCES TO RELATED APPLICATIONS

This application is a non-provisional of, and claims the benefit of the filing date of U.S. Prov. Patent Appl. No. 60/804,261, entitled "SELECTIVE RENAL CANNULATION AND INFUSION SYSTEMS AND METHODS, filed Jun. 8, 2006, the entire disclosure of which is incorporated herein by reference for all purposes.

BACKGROUND OF THE INVENTION

Embodiments disclosed herein pertain generally to medical device systems and methods for delivering treatment to internal body lumens. More specifically, embodiments are related to intra aortic renal treatment delivery systems and methods.

Many different medical device systems and methods have been previously described for locally delivering fluids or other agents into various body regions, including body lumens such as vessels, or other body spaces such as organs or heart chambers. Local fluid delivery systems may include drugs or other agents, or may even include locally delivering the body's own fluids, such as artificially enhanced blood transport, for example either entirely within the body such as directing or shunting blood from one place to another, or in extracorporeal modes such as via external blood pumps and the like. Local agent delivery systems are herein generally intended to relate to introduction of a foreign composition as an agent into the body, which may include drugs or other useful or active agents, and may be in a fluid form or other form such as gels, solids, powders, gases, and the like.

In general, local agent delivery systems and methods are often used for the benefit of achieving relatively high, localized concentrations of agent where injected within the body in order to maximize the intended effects there and while minimizing unintended peripheral effects of the agent elsewhere in the body. Where a particular dose of a locally delivered agent may be efficacious for an intended local effect, the same dose systemically delivered would be substantially diluted throughout the body before reaching the same location. The agent's intended local effect is equally diluted and efficacy is compromised. Thus systemic agent delivery requires higher dosing to achieve the required localized dose for efficacy, often resulting in compromised safety due to for example systemic reactions or side effects of the agent as it is delivered and processed elsewhere throughout the body other than at the intended target.

In some cases, patients may present arterial anatomical features that provide challenges to operators who wish to administer treatment to the patient. For example, in some patients there is substantial offset between renal arteries that may make simultaneous bilateral renal artery cannulation difficult. Relatedly, some patients may only have one renal artery, or may only require treatment in one of their two renal arteries. What is needed are improved systems and techniques that allow physicians and other medical personnel to efficiently and effectively treat such patients. Embodiments described herein provide solutions for at least some of such needs.

BRIEF SUMMARY OF THE INVENTION

Embodiments of the present invention provide flexible approaches that can easily be adapted for use in treating patients having certain vascular physiological features such as offset renal arteries or singular renal arteries. These approaches are also well suited for use with patients having two renal arteries who require treatment in only one of the arteries. Advantageously, with the incorporation of improved delivery catheter configurations and infusion catheter geometries, it is possible to provide selective renal cannulation and infusion techniques for use by physicians in treating an important patient population.

In a first aspect, embodiments of the present invention include a renal infusion system. The renal infusion system includes an infusion catheter having a bifurcated distal end with a first branch and second branch. The branches are biased to deploy laterally when unconstrained. The system also includes a delivery sheath having a lumen which receives the infusion catheter and constrains the first branch and second branch. A distal opening of the delivery sheath is formed asymmetrically to allow one of the first and second branches to open laterally while the other of the branches remains constrained. The distal opening can include an elongate structure on one side of the sheath and be free from a constraining structure on the other side of the sheath. In some cases, the distal opening is chamfered. The symmetric distal opening can have an axial deployment window opposite to a solid wall. In some aspects, the delivery sheath has a lateral protrusion proximal and diametrically opposite to the axial deployment window. The protrusion can balance a force caused by deployment of a single branch of the infusion catheter. The delivery sheath may include a detectable marker disposed adjacent the distal opening. In a related aspect, the delivery sheath includes a first detectable marker disposed proximally adjacent to the distal opening and a second detectable marker disposed laterally adjacent to the distal opening. The first detectable marker may be disposed on a first side of the sheath and the second detectable marker may be disposed on a second side of the sheath that is opposite to the first side. In some aspects, the delivery sheath includes a semi-circular curve disposed proximal to the distal opening, such that an arc of the semi-circular curve projects in a first direction, and the distal opening faces a second direction opposite to the first direction. The renal infusion system can also include an attachment means configured to secure the delivery sheath with a vessel access site of a patient.

In another aspect, embodiments of the present invention include a method of deploying an infusion catheter in a patient. The method includes positioning a delivery sheath within an aorta of the patient, the delivery sheath having a distal opening, advancing a first branch of the infusion catheter through the distal opening of the delivery sheath while preventing advancement of the second branch of the infusion catheter through the distal opening, advancing the second branch of the infusion catheter through the distal opening of the delivery sheath, directing the first branch of the infusion catheter toward a first renal artery of the patient, and directing the second branch of the infusion catheter toward a second renal artery of the patient. The method can also include balancing a force caused by advancement of the first branch with a lateral protrusion of the delivery sheath, wherein the distal opening comprises an axial deployment window, and the lateral protrusion is disposed proximal and diametrically opposite to the axial deployment window. In some cases, the method includes visualizing a position of a distal opening marker relative to the patient. In related cases, the method includes securing the delivery sheath with a vessel access site of the patient with an attachment means.

In still another aspect, embodiments of the present invention encompass an infusion catheter that includes a catheter body having a distal end with a first branch, where the branch is biased to deploy laterally when unconstrained. The catheter also includes a first valve structure disposed between a main lumen in the catheter body and a branch lumen in the first branch, where the first valve structure is closed when the first branch is undeployed and opens in response to lateral deployment of the first branch. The distal end can be bifurcated and can include a second branch that is biased to deploy laterally when unconstrained. The infusion catheter may include a second valve structure disposed between the main lumen and a branch lumen in the second branch, where the second valve structure is closed when the second branch is undeployed and opens in response to lateral deployment of the second branch. In some cases, the first valve includes a two-way valve. In some cases, the first valve includes a pressure regulated valve that remains closed when a distal side fluid pressure is greater than an aortic blood pressure of the patient. The first branch may be longer than the second branch.

In another aspect, embodiments of the present invention encompass a method of deploying an infusion catheter in a patient, that includes advancing a catheter body into an aorta of the patient, where the catheter body includes a distal end with a first branch, and the branch is biased to deploy laterally when unconstrained. The method can also include altering flow volume in a first flow path that passes through the first branch by moving the first branch between a constrained configuration and a laterally deployed configuration. In some cases, moving the first branch toward the laterally deployed configuration includes moving the first branch toward a first renal artery. In related cases, the catheter body is bifurcated and includes a second branch that is biased to deploy laterally when unconstrained, and the method includes altering flow volume in a second flow path that passes through the second branch by moving the second branch between a constrained configuration and a laterally deployed configuration. In some aspects, moving the second branch toward the laterally deployed configuration includes moving the second branch toward a second renal artery. The method can also encompass moving the first branch toward the laterally deployed configuration prior to moving the second branch toward the laterally deployed configuration. In related aspects, the method involves moving the first branch toward the laterally deployed configuration concurrently with moving the second branch toward the laterally deployed configuration.

In yet another aspect, embodiments of the present invention involve a method of deploying a renal infusion system in a patient having offset real arteries. The method includes positioning a delivery sheath of the infusion system within an aorta of the patient, advancing a first catheter branch of the infusion system through a deployment window of the delivery sheath toward a first renal artery, regulating a first valve to alter a first flow path that passes through the first catheter branch toward the first renal artery, advancing a second catheter branch of the infusion system through the deployment window of the delivery sheath toward a second renal artery, and regulating a second valve to alter a second flow path that passes through the second catheter branch toward the second renal artery. In some aspects, regulating the first valve includes adjusting the first branch from a constrained configuration toward a released configuration. The method can also include restraining the first branch in the constrained configuration with the delivery sheath prior to or subsequent to advancing the first branch through the deployment window. In some cases, adjusting the first branch from a constrained configuration toward a released configuration involves expanding a fluid lumen of the first branch. Regulating the first valve may occur concurrently with advancing the first branch through the deployment window. In related aspects, regulating the first valve includes adjusting the first branch from a released configuration toward a constrained configuration.

In another aspect, embodiments of the present invention encompass a method of deploying a renal infusion system in a patient that includes positioning a delivery sheath of the infusion system within an aorta of the patient such that a deployment window of the delivery sheath is disposed near a first renal artery and a second renal artery of the patient, advancing a first catheter branch of the infusion system through the deployment window toward the first renal artery, regulating a first branch valve to alter a first flow path that passes through the first catheter branch toward the first renal artery, and retaining a second catheter branch of the infusion system within the delivery sheath. The method can also include advancing the second catheter branch of the infusion system through the deployment window toward the second renal artery, and regulating a second branch valve to alter a second flow path that passes through the second catheter branch toward the second renal artery. Advancing the first catheter branch and advancing the second catheter branch may occur concurrently. In a related aspect, the method includes visualizing a position of a deployment window marker relative to the patient.

In still another aspect, embodiments of the present invention encompass a renal infusion system that includes a delivery sheath configured for placement within an aorta of a patient. The delivery sheath may include a deployment window. The system may also include a first catheter branch configured for advancement through the deployment window of the delivery sheath toward a first renal artery of the patient, and a first flow path that passes through the first catheter branch. The first flow path may be configured to provide a first fluid flow toward the first renal artery. The system may further include a first valve that regulates the first flow path, a second catheter branch configured for advancement through the deployment window of the delivery sheath toward a second renal artery of the patient, and a second flow path that passes through the second catheter branch. The second flow path may be configured to provide a second fluid flow toward the second renal artery. The system may also include a second valve that regulates the second flow path. In some aspects, the delivery sheath includes a marker disposed near the deployment window. In related aspects, the first branch may embody a constrained configuration and a released configuration, where the first fluid flow through the first flow path is greater when the first branch is in the released configuration than when it is in the constrained configuration. In some cases, the first branch is in a constrained configuration when disposed within the delivery sheath, and is in a released configuration when advanced through the deployment window. The first valve can include a first notch valve that constricts the first flow path when the first branch is in a constrained configuration, and that dilates the first flow path when the first branch is in a released configuration. In related aspects, the delivery sheath includes a semi-circular curve disposed proximal to the deployment window, such that an arc of the semi-circular curve projects in a first direction, and the deployment window faces a second direction opposite to the first direction. The first branch may include a marker. The first valve may include a two-way valve. In some aspects, the first valve includes a pressure regulated valve that remains closed when a distal side fluid pressure is greater than an aortic blood pressure of the patient. The system may also include an attachment means configured to secure the delivery sheath with a vessel access site of the patient. In some cases, the first catheter branch can be longer than the second catheter branch.

For a fuller understanding of the nature and advantages of the present invention, reference should be had to the ensuing detailed description taken in conjunction with the accompanying drawings.

BRIEF DESCRIPTION OF THE DRAWINGS

FIGS. 5A and 5B show a renal infusion system according to embodiments of the present invention.

DETAILED DESCRIPTION OF THE INVENTION

The description herein, relates to medical material delivery systems and methods in the context of their relationship in use within a patient's anatomy. Accordingly, for the purpose of providing a clear understanding, the term proximal should be understood to mean locations on a system or device relatively closer to the operator during use, and the term distal should be understood to mean locations relatively further away from the operator during use of a system or device. The present embodiments herein therefore generally relate to local renal drug delivery or perfusion generally from the aorta; however, it is contemplated that these systems and methods may be suitably modified for use in other anatomical regions and for other medical conditions without departing from the broad scope of the various aspects as illustrated by the embodiments.

In general, the disclosed material delivery systems will include a fluid delivery assembly, a proximal coupler assembly and one or more elongated bodies, such as tubes or catheters. These elongated bodies may contain one or more lumens and generally consist of a proximal region, a mid-distal region, and a distal tip region. The distal tip region will typically have means for delivering a material such as a fluid agent. It is appreciated, however, that the present systems may be configured to deliver any of a wide variety of treatment modalities, including the therapeutic application of ultrasound and other types of treatment energy. Radiopaque markers or other devices may be coupled to the specific regions of the elongated body to assist introduction and positioning.

The material delivery system is intended to be placed into position by a physician, typically either an interventionalist (e.g. a cardiologist or radiologist) or an internist, a physician who specializes in the treatment of intensive-care patients. The physician can gain access to a femoral artery in the patient's groin, typically using a Seldinger technique of percutaneous vessel access or other conventional method.

For additional understanding, further more detailed examples of other systems and methods for providing local renal drug delivery are variously disclosed in the following published references: WO 00/41612 to Keren et al.; and WO 01/83016 to Keren et al. The disclosures of these references are herein incorporated in their entirety by reference thereto. Moreover, various combinations with, or modifications according to, various aspects of the present embodiments as would be apparent to one of ordinary skill upon review of this disclosure together with these references are also considered within the scope of invention as described by the various independently beneficial embodiments described below.

Figure 1:
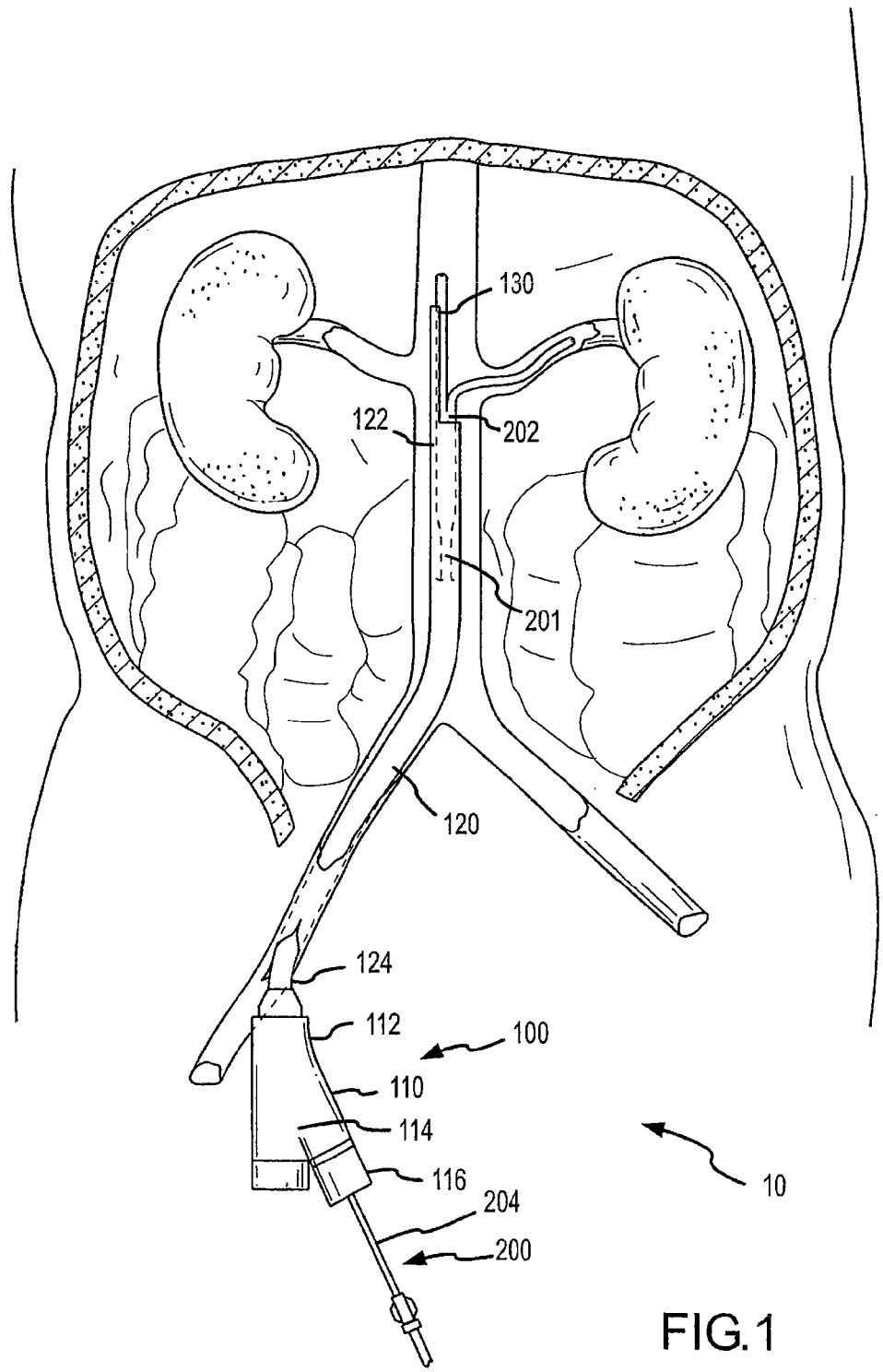
FIG. 1 illustrates a renal infusion system according to embodiments of the present invention.

Turning now to the drawings, FIG. 1 illustrates a renal infusion system 10 according to one embodiment of the present invention. System 10 includes an introducer assembly 100 and a renal delivery or infusion catheter 200. Introducer assembly 100 can have a Y-hub 110 and a delivery sheath 120. Typically, Y-hub distal end 112 is coupled with delivery sheath proximal end 124. Infusion catheter 200 includes an infusion catheter shaft 201 having a bifurcated distal end 202 and a proximal end 204. Infusion catheter shaft 201 can be disposed within introducer assembly 100, such that infusion catheter shaft distal end 202 can extend and retract from a distal opening 130 of delivery sheath distal end 122, and infusion catheter shaft proximal end 204 can extend from a first port 116 of Y-hub proximal end 114. In some embodiments, distal opening 130 is formed asymmetrically to allow an infusion branch to deploy laterally while another infusion branch remains undeployed, constrained within the sheath. Delivery sheath 120 can have a length selected to terminate at or near the renal arteries. The length of delivery sheath 120 from proximal end 124 to distal end 122 can be in the range from about 20 cm to about 50 cm, and optionally from about 30 cm to about 45 cm. In some cases, the outer diameter of delivery sheath 120 may be, for example, less than or equal to 2 French greater than its inner diameter. In other cases, the outer diameter may be about 3 French greater than the inner diameter. In related cases, the difference between the outer diameter of delivery sheath 120 and its inner diameter may be within the range of between about 0.015 inches to about 0.025 inches. Renal infusion system 10 is also suitable for use with supplemental catheters such as coronary guide catheters or peripheral guide catheters as described in, for example, U.S. patent application Ser. No. 11/241,749 filed Sep. 29, 2005, the contents of which are hereby incorporated by reference.

Figure 2A:
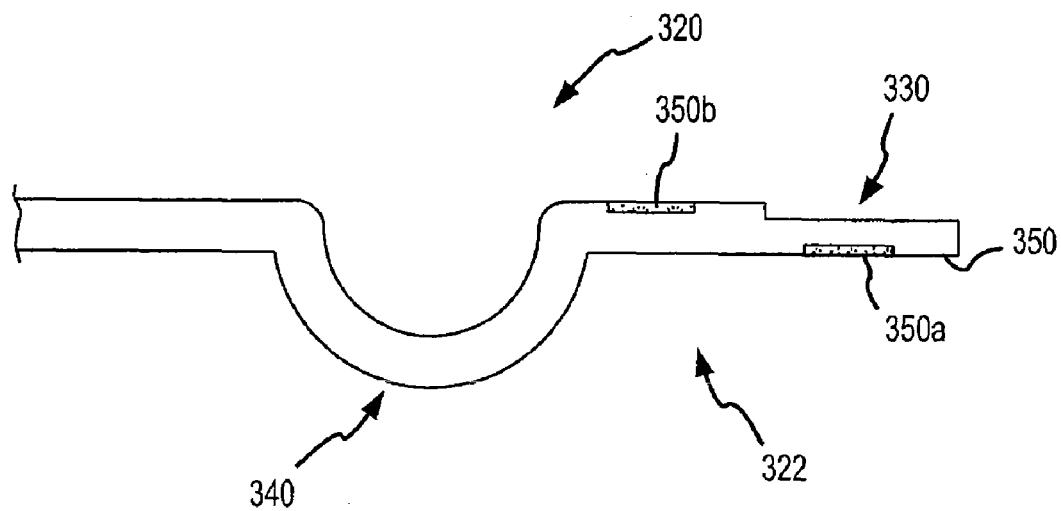
FIGS. 2A and 2B illustrate a delivery sheath according to embodiments of the present invention.

FIG. 2A shows one embodiment of a delivery sheath 320. As depicted here, delivery sheath 320 includes a distal opening or notch 330 that allows extension and retraction of an infusion catheter (not shown) therethrough. Distal opening 330 defines an asymmetric opening having an axial deployment window on one side, and a wall, constraining structure, or elongate structure 350 on an opposite side. Wall 350 may be constructed of a solid material or any other suitable material. Distal opening 330 may be implemented via any of a variety of design choices. For example, distal opening 330 may be embodied by a thin rectangular cut-out having a long edge parallel to a longitudinal axis of deliver sheath 320, and a short edge sized slightly greater than the outer diameter of a single infusion catheter branch (not shown) and terminating coincidentally at the distal tip of sheath 320. In some embodiments, distal opening 330 may be chamfered. As a delivery or infusion catheter (not shown) is advanced distally through an interior space or lumen of sheath 320, distal opening can thus provide a window for deployment of an infusion catheter branch before it reaches the true end of sheath 320. Typically the window or opening is free from a constraining structure. Because distal opening 330 confers a break in the stress that would occur during application of torque or imposed bending by vessel anatomy on sheath 320, the remaining material circumferentially adjacent to distal opening 330 bears the added stress. To reduce the kinking or luminal collapse that could occur within the elevated stress zone, the section of sheath 320 adjacent to distal opening 330 can be constructed of a stiff material. In some cases, this material includes Pebax®, nylon, polytetrafluoroethylene (PTFE) or the like, having a higher durometer as compared to the material used to construct other portions of sheath 320. In some cases, the stiff material includes a section of the wall opposite to the deployment window, and also includes other sections of sheath 320. For example, the entire sheath distal end 322, or a significant portion thereof, may include a stiff material. In some embodiments, the stiff material section can occur 1 mm to 4 mm proximal to the start of the deployment window, and terminate at the distal end of the sheath. The stiff section can provide mechanical stability to the distal tip section of the sheath bearing the deployment window during delivery and dwell of the sheath by ensuring that the build up of stress resulting from the absence of supporting material at the deployment window is compensated for by the stiffer material. Thus, stress from vessel anatomy, inner members, or operator manipulation can be tolerated, and collapse of the window can be prevented.

Delivery sheath 320 can include detectable markers adjacent to distal opening 330. Here, delivery sheath 320 includes a first detectable marker 350*a* disposed on the side of sheath 320 opposite to distal opening 330, and a second detectable marker 350*b* disposed proximal to distal opening 330. Detectable markers 350*a*, 350*b* may include, for example, a radiopaque agent such as barium, tungsten, gold, platinum, iridium, palladium, rhodium, and the like. During a surgical or diagnostic procedure, detectable markers such as these can assist a clinician in identifying or visualizing the position of the distal tip of sheath 320, and the orientation of distal opening 330 relative to the surrounding patient anatomy and the center of sheath 320. In an exemplary embodiment, one rectangular marker is located at the proximal base of the distal opening with the long edge of the marker oriented parallel to the longitudinal axis of the sheath, and a second marker of the same shape and orientation is positioned on the side of the sheath opposing the distal opening, with the distal edge of the second marker lined up with the distal end of the sheath.

Delivery sheath 320 can also include a semi-circular curve or protrusion 340, which can have an arc that extends laterally from a central longitudinal axis of the sheath. In some embodiments, curve 340 terminates proximal to distal opening 330 and is disposed or projects in a direction opposite to that of the side of distal opening 330. Curve 340 can facilitate kinematic support and stability of a distal end 322 of sheath 320 during single or asynchronous bilateral renal artery cannulation, and other procedures described herein. For example, a curve or protrusion of the sheath can balance a force caused by deployment of a branch of the infusion catheter.

Figure 2B:
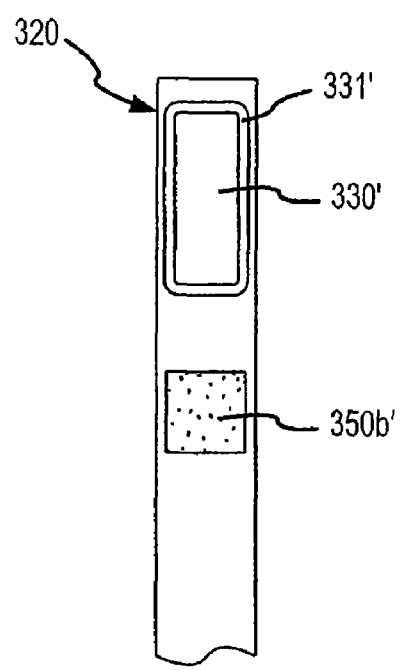

FIG. 2B shows one embodiment of a delivery sheath 320'. As depicted here, delivery sheath 320' includes a distal opening or window 330' that allows extension and retraction of an infusion catheter (not shown) therethrough. Distal opening 330' defines an asymmetric opening having an axial deployment window on one side, and a constraining structure on an opposite side. As shown here, window 330' is surrounded by a frame 331'. Detectable marker 350*b*' is disposed proximally adjacent to window 330'.

Figures 3A, 3B:
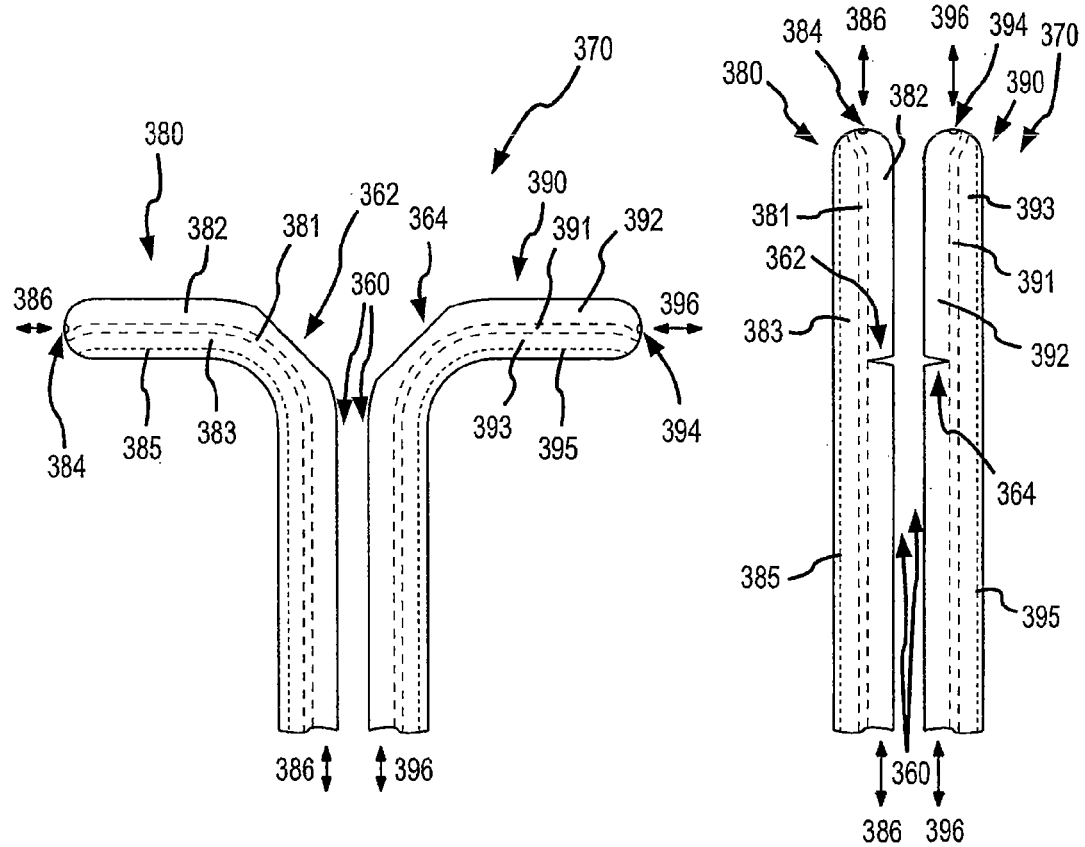
FIGS. 3A and 3B illustrate an infusion catheter according to embodiments of the present invention.

FIGS. 3A and 3B illustrate an embodiment of an delivery catheter valve means 360. Delivery or infusion catheter 370 includes a first infusion catheter branch 380 and a second infusion catheter branch 390. FIG. 3A shows infusion catheter 370 in a bilaterally deployed configuration. First notch or kink point 362 is in an open position or unkinked configuration, such that first branch infusion lumen 382 defines an open first flow path 386. Lumen 382 is open to flow, but may be somewhat restricted at the kink point due to a reduced flow diameter or cross section. In some embodiments, notch 362 in the open configuration is defined by a flat or straight surface along the curvature of branch 380. In use, infusion fluid can be delivered through first branch lumen 382 and first branch port 384 into the patient. Similarly, second notch or kink point 364 is in an open position or unkinked configuration, such that second branch infusion lumen 392 defines an open or less restricted second flow path 396. Lumen 392 is open to flow, but in some cases may be slightly narrower at the kink point. In some embodiments, notch 364 in the open configuration is defined by a flat or straight surface along the curvature of branch 390. In use, infusion fluid can be delivered through second branch infusion lumen 392 and second branch port 394 into the patient. In some embodiments, branches 380, 390 are biased to deploy laterally when unconstrained. This bias may be caused or assisted by support members 385 and 395 situated within support lumens 383 and 393, respectively. For example, support members 385, 395 can include a metal wire ribbon, or some other component that compels branches 380, 390 to deploy or bend laterally. Lumens 382 and 383 can be separated by a luminal divide 381, and lumens 392 and 393 can be separated by a luminal divide 391.

FIG. 3B shows infusion catheter 370 in an undeployed configuration. First notch or kink point 362 is in a closed position or kinked configuration, such that first branch infusion lumen 382 defines a closed or more restricted first flow path 386. In use, infusion fluid can be prevented or inhibited from flowing through first branch infusion lumen 382 and first branch port 384 into the patient. Similarly, second notch 364 is in a closed position, such that second branch infusion lumen 392 defines a closed second flow path 396. The kink point, which was flat in the open configuration (see FIG. 3A) is now kinked due to straightening of the branch. In use, infusion fluid can be prevented or inhibited from flowing through second branch infusion lumen 392 and second branch port 394 into the patient. Thus, valve means such as the notch or kink point can operate to regulate or alter flow volume through the lumen or flow path as desired. In some embodiments, this regulation can be determined by the extent to which a branch is deployed. For example, a notch valve in the branch can completely constrict the flow path when the branch is completely constrained, can partially constrict the flow path when the branch is partially constrained, and can completely dilate the flow path when the branch is completely unconstrained or deployed.

The mechanism of the infusion valve within the branch, therefore, may involve a double lumen branch. The laterally disposed lumens (e.g. 382, 392) can be configured for a fluid infusion function, and the medially disposed lumens (e.g. 383, 393) can be configured for support or bias function. In some embodiments, the branches include kink points such that when a branches is in the curved configuration, the kink point is not entirely collapsed, however, the lumen at this point is constricted because the branch luminal wall on the longer face of the curve has a straight section at the kink point that reduces the luminal cross section. When the branch is constrained in a delivery sheath, for example, this section of the branch luminal wall on the longer face of the curve collapsed, and serves as a barrier or impediment to luminal fluid flow.

In related embodiments, delivery catheter 370 as depicted in FIG. 3A is in an unconstrained configuration, and delivery catheter as depicted in FIG. 3B is in a constrained configuration. In some embodiments, branch infusion lumens 382, 392 have an ovular cross-sectional profile, and are disposed medially, toward the outer longer edge or greater arc of a curve in branches 380, 390, respectively. In some cases, the valve means can include a radially-inward notch that facilitate stress localization and collapse of the branch infusion lumen at the notch section, when the branch is in a constrained or otherwise undeployed configuration.

Embodiments provided herein include selective renal cannulation and infusion systems that can be used in a variety of clinical scenarios. For example, for patients having moderate to highly offset renal artery anatomies, where synchronous one-step cannulation may be difficult, embodiments may be used to selectively cannulate the renal arteries with independent control of the deployment of either delivery catheter branch. Embodiments may also be used in clinical circumstances where cannulation and infusion through a single renal artery is desired, for example in patients having one kidney or where treatment is desired for only one of two kidneys. Embodiments can also be used in bilateral renal cannulation of patients having zero or minimal offset in the anatomy of the renal arteries. In such cases, embodiments can allow for simultaneous one-step cannulation. Valve means may include one-way or two-way valves. In some instances, valve means may include pressure-regulated valves.

Asynchronous Delivery to Offset Renal Arteries

In some clinical circumstances, the degree of offset between the right and left renal arteries may present difficulties or obstacles to a single-step synchronous bilateral renal artery cannulation procedure. An embodiment shown in FIGS. 4A, 4B, and 4C can overcome such obstacles by allowing for a two-step asynchronous bilateral cannulation of the renal arteries. In this scheme, a first renal artery is cannulated with a first branch of the infusion catheter while a second branch of the infusion catheter remains undeployed, constrained by the delivery sheath. Thereafter, the second renal artery is cannulated with the second branch of the infusion catheter.

Figure 4A:
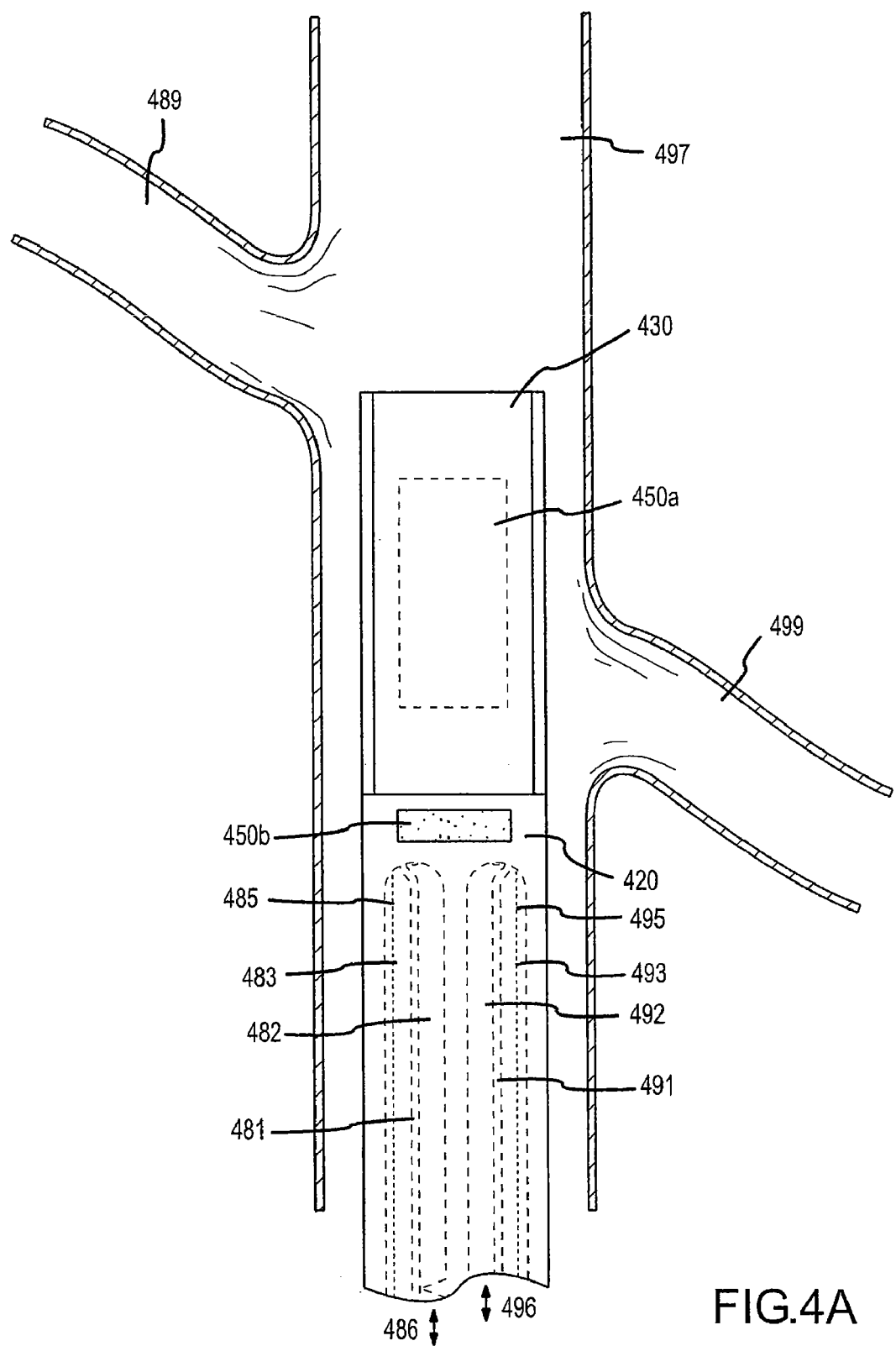
FIGS. 4A, 4B, and 4C show a renal infusion system according to embodiments of the present invention.

In the embodiment illustrated in FIG. 4A, delivery sheath 420 is positioned within an aorta of a patient such that a face of window 430 is oriented at or about a right angle from proximal renal artery 499 or distal renal artery 489. Under fluoroscopy, delivery sheath 420 can be positioned in the patient's aorta 497 such that a radiopaque proximal marker 450b, indicating a proximal end of deployment window 430, is just below or proximal to proximal renal artery 499. In some embodiments, each of the separate branches can be coupled with its own catheter, so they may be individually and separately advanced and retracted within the delivery sheath. An infusion catheter is disposed within delivery sheath 420, such that first infusion catheter branch 480 and second infusion catheter branch 490 are disposed proximal to deployment window 430, in a constrained undeployed configuration. First branch infusion lumen 482 defines a closed first flow path 486, and second branch infusion lumen 492 defines a closed second flow path 496. The infusion catheter can include support members 485 and 495 situated within support lumens 483 and 493. The infusion catheter can also include a luminal divide 481 separating lumens 482 and 483, and a luminal divide 491 separating lumens 492 and 493.

Figure 4B:
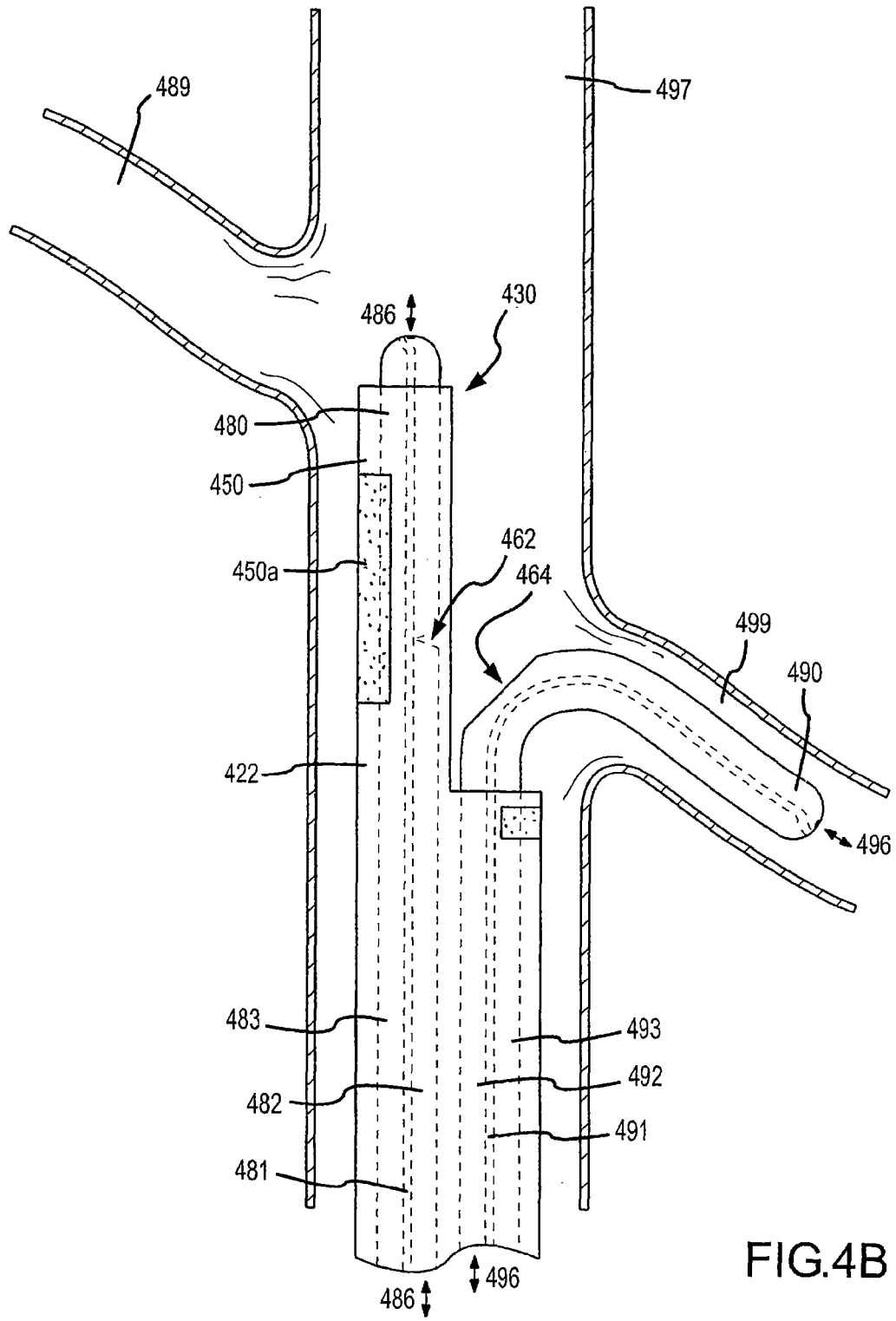

As shown in FIG. 4B, delivery sheath 420 can be rotated, as necessary, to position radiopaque distal marker 450a near or toward distal renal artery 489, on the side of aorta 497 opposite to proximal renal artery 499. In this embodiment, such manipulation orients the face of deployment window 430 to point toward proximal renal artery 499. The bifurcated infusion catheter can be advanced distally through delivery sheath 420, such that second infusion catheter branch 490 exits laterally through deployment window 430 and into or toward proximal renal artery 499 while first infusion catheter branch 480 remains constrained by wall 422 of delivery sheath 420. In some cases, the branches may be biased toward lateral deployment in opposing directions. This bias may facilitate advancement of branch 480 through window 430 toward artery 499, while at the same time lateral advancement of branch 480 is prevented by wall 450.

The position of delivery sheath 420, the bifurcated infusion catheter, or both, may be adjusted to facilitate cannulation of second branch 490 into proximal renal artery 499. During this interim, where first infusion catheter branch 480 is constrained and second infusion catheter branch 490 is cannulated, the infusion valve means prevents or inhibits infusion through first infusion catheter branch 480 which can minimize systemic side-effects, while at the same time permits infusion through second infusion catheter branch 490. As shown here, lateral deployment of second infusion catheter branch 490 opens infusion valve 464 and permits infusion into proximal renal artery 499. Thus, first branch infusion lumen 482 defines a closed first flow path 486, and second branch infusion lumen 492 defines an open second flow path 496 that allows infusion or delivery to proximal renal artery 499. A curve or protrusion in the delivery sheath (see FIG. 2) can provide support to keep the second infusion catheter branch from falling out of the proximal renal artery prior to cannulation of the first infusion catheter branch. For example, the curve or protrusion can balance a force caused by deployment of the second branch.

Figure 4C:
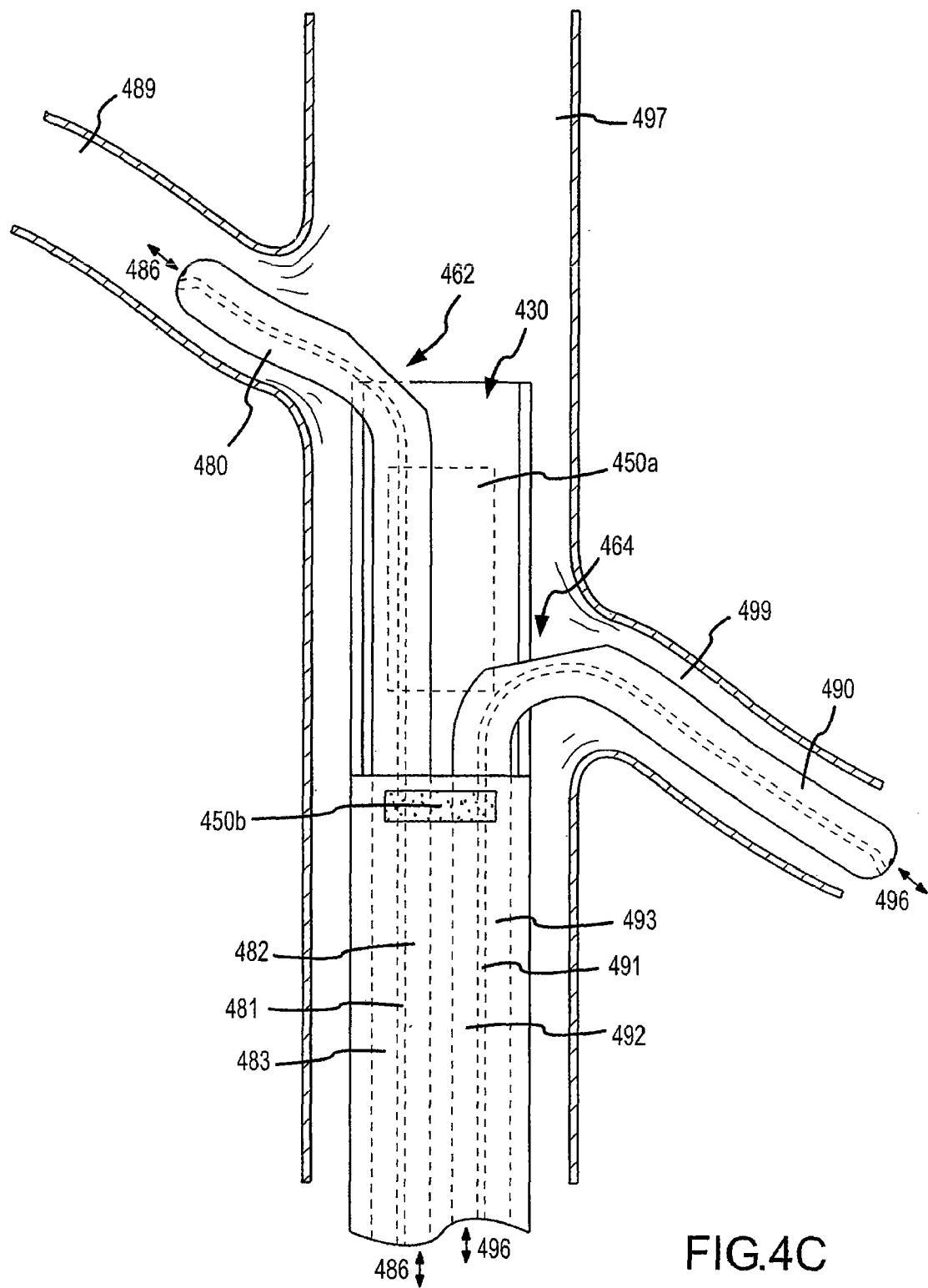

To deploy first infusion catheter branch 480 to distal renal artery 489, the distal end of delivery sheath 420 is positioned just below or proximal to distal renal artery 489 as illustrated in FIG. 4C. Depending on the degree of offset between the renal arteries, the infusion catheter can be slightly retracted or advanced to deploy first infusion catheter branch 480 at distal renal artery 489. As shown here, lateral deployment of first infusion catheter branch 480 through the deployment window opens infusion valve 462 and permits infusion into distal renal artery 489. Accordingly, in full deployment, first branch infusion lumen 482 defines an open first flow path 486 that allows infusion or delivery to distal renal artery 489, and second branch infusion lumen 492 defines an open second flow path 496 that allows infusion or delivery to proximal renal artery 499.

Delivery to Single Renal Artery

In some clinical circumstances, for example in cases of patients having only one kidney, it may be desirable to infuse only a single renal artery. An embodiment shown in FIGS. 5A and 5B allows for unilateral cannulation of a single renal artery. In this scheme, the sole renal artery is cannulated with a first branch of the infusion catheter while a second branch of the infusion catheter remains undeployed, constrained by the delivery sheath. This embodiment also allows for unilateral cannulation of a single artery in a patient having two kidneys, where treatment of only one kidney is desired.

In the embodiment illustrated in FIG. 5A, delivery sheath 520 is positioned such that a face of window 530 is oriented at or about a right angle from proximal renal artery 599. Under fluoroscopy, delivery sheath 520 can be positioned in the patient's aorta 597 such that a radiopaque proximal marker 450b, indicating a proximal end of deployment window 530, is just below or proximal to proximal renal artery 599. An infusion catheter is disposed within delivery sheath 520, such that first infusion catheter branch 580 and second infusion catheter branch 590 are disposed proximal to deployment window 530, in a constrained undeployed configuration. First branch lumen 582 defines a closed first flow path 586, and second branch lumen 592 defines a closed second flow path 596.

As shown in FIG. 5B, delivery sheath 520 can be rotated under fluoroscopy to position radiopaque distal marker 550a near or toward the side of aorta 597 opposite to proximal renal artery 599. In this embodiment, such manipulation orients the face of deployment window 530 to point toward proximal renal artery 599. The bifurcated infusion catheter can be advanced distally through delivery sheath 520, such that second infusion catheter branch 590 exits laterally through deployment window 530 and into or toward proximal renal artery 599 while first infusion catheter branch 580 remains constrained by wall 522 of delivery sheath 520. The position of delivery sheath 520, the bifurcated infusion catheter, or both, may be adjusted to facilitate cannulation of second branch 590 into proximal renal artery 599. During this interim, where first infusion catheter branch 580 is constrained and second infusion catheter branch 590 is cannulated, the infusion valve means prevents or inhibits infusion through first infusion catheter branch 580 which can minimize systemic side-effects that could otherwise occur due to infusive flowing into the aorta, while at the same time permits infusion through second infusion catheter branch 590. The constrained configuration of first infusion catheter branch 580 can also mitigate risk of injury to the aortic wall that could otherwise occur if it were deployed unnecessarily. As shown here, lateral deployment of second infusion catheter branch 590 opens infusion valve 564 and permits infusion into proximal renal artery 599. Thus, first branch infusion lumen 582 defines a closed first flow path 586, and second branch infusion lumen 592 defines an open second flow path 596 that allows infusion or delivery to the target proximal renal artery 599. A curve or protrusion in the delivery sheath (see FIG. 2) can help push the distal end or tip of the delivery sheath toward the target renal artery, thus maintaining the cannulated branch within the target renal artery. In some embodiments, the infusion catheter can include support members 585 and 595 situated within support lumens 583 and 593. The infusion catheter can also include a luminal divide 581 separating lumens 582 and 583, and a luminal divide 591 separating lumens 592 and 593.

Simultaneous Delivery to Renal Arteries

Figure 6A:
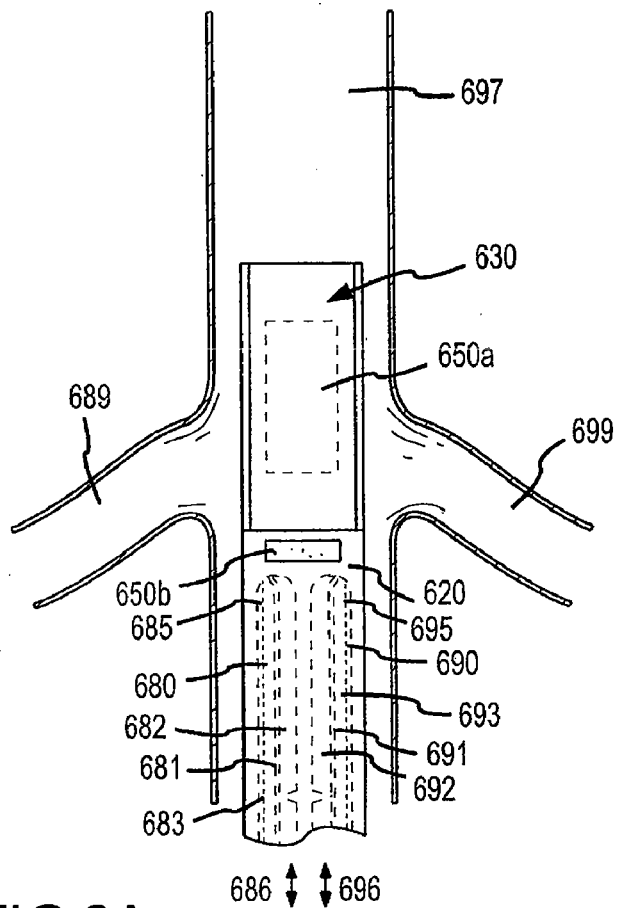
FIGS. 6A and 6B show a renal infusion system according to embodiments of the present invention.
Figure 6B:
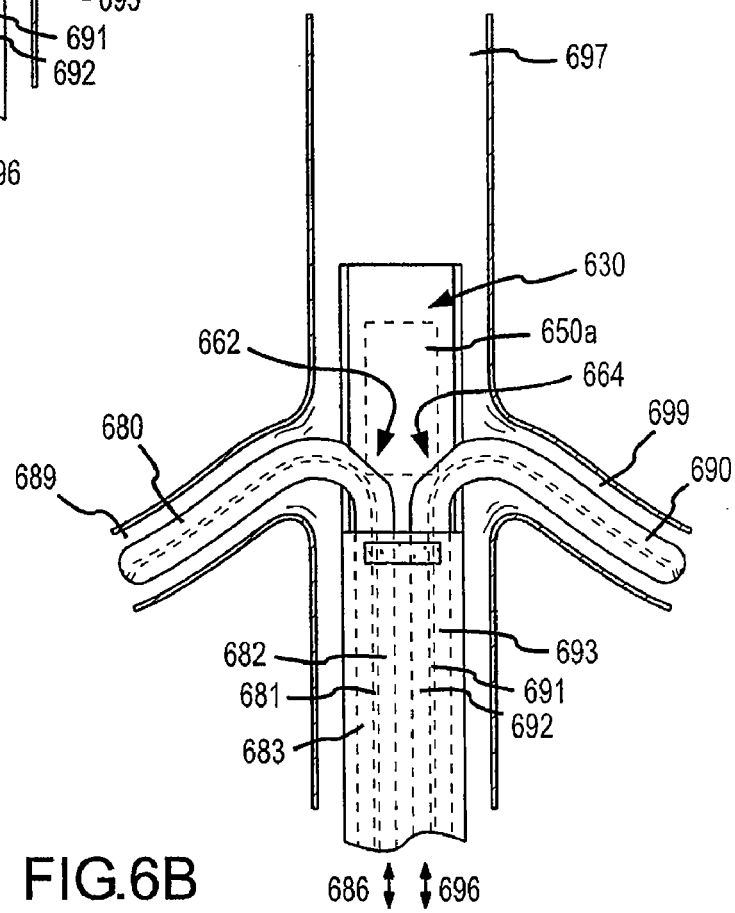

An embodiment shown in FIGS. 6A and 6B allows for simultaneous bilateral cannulation of two renal arteries, which is often useful in clinical circumstances where a patient presents minimal or no lateral offset of the renal arteries.

In the embodiment illustrated in FIG. 6A, delivery sheath 620 is positioned such that a face of window 630 is oriented at or about a right angle from first renal artery 689 or second renal artery 699. Under fluoroscopy, delivery sheath 620 can be positioned in the patient's aorta 697 such that a radiopaque proximal marker 650b, indicating a proximal end of deployment window 630, is just below or proximal to renal arteries 689, 699. An infusion catheter is disposed within delivery sheath 620, such that first infusion catheter branch 680 and second infusion catheter branch 690 are disposed proximal to deployment window 630, in a constrained undeployed configuration. First branch lumen 682 defines a closed first flow path 686, and second branch lumen 692 defines a closed second flow path 696.

As shown in FIG. 6B, the bifurcated infusion catheter can be advanced distally through delivery sheath 620, such that first infusion catheter branch 680 exits laterally through deployment window 630 and into or toward first renal artery 689, and second infusion catheter branch 690 exits laterally through deployment window 630 and into or toward proximal renal artery 699. As shown here, lateral deployment of first infusion catheter branch 680 opens infusion valve 662 and permits infusion into first renal artery 689, and lateral deployment of second infusion catheter branch 690 opens infusion valve 664 and permits infusion into second renal artery 699. Thus, first branch infusion lumen 682 defines an open first flow path 686, and second branch infusion lumen 692 defines an open second flow path 696 that allows infusion or delivery to first and second renal arteries, respectively. In this way, a bifurcated infusion catheter can be advanced to concurrently deploy both branches and achieve bilateral renal artery cannulation. In some embodiments, the infusion catheter can include support members 685 and 695 situated within support lumens 683 and 693. The infusion catheter can also include a luminal divide 681 separating lumens 682 and 683, and a luminal divide 691 separating lumens 692 and 693.

Figure 7:
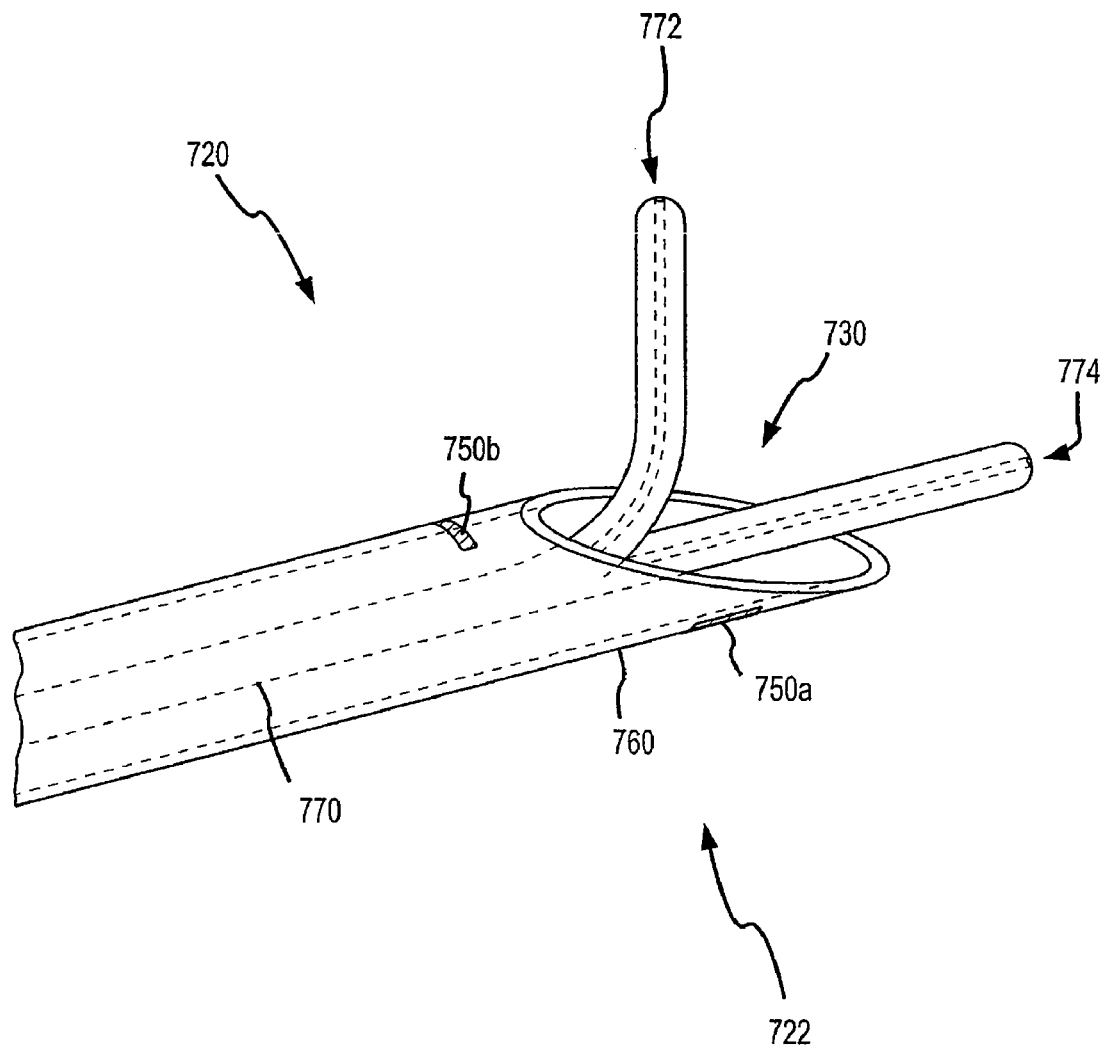
FIG. 7 depicts a renal infusion system according to embodiments of the present invention.

As noted previously, a delivery sheath can include a distal opening that allows extension and retraction of an infusion catheter therethrough. As depicted in FIG. 3, a distal opening or window can define a plane that is aligned with a central longitudinal axis of the delivery sheath. FIG. 7 shows another embodiment of a delivery sheath 720, where a distal end 722 of delivery sheath 720 is cut at a skewed angle or otherwise manufactured to provide a skewed opening. Thus, the distal opening or window defines a plane that is angularly offset from a central longitudinal axis of the delivery sheath. Delivery sheath 720 includes a distal opening 730 that allows extension and retraction of first 772 and second 774 branches of an infusion catheter 770 therethrough. Distal opening 730 defines an asymmetric opening having a deployment window on one side, and a wall 760 on an opposite side. The wall may be constructed of a solid material or any other suitable material. Distal opening 730 may be implemented, therefore, as a delivery sheath 720 that is cut at a skewed angle, and the skewed edge can provide similar functionality as that provided by other configurations, for example the slit-shaped distal opening shown in FIG. 3. First branch 772 can be deployed from delivery sheath 720 while second branch 774 is held constrained by distal end 722 of delivery sheath 720, against the sheath tip material on the opposing side of the sheath lumen. Second branch 774 can be deployed by advancing it beyond the distal end of the edge of opening 730.

As delivery or infusion catheter 770 is advanced distally through an interior space or lumen of delivery sheath 720, distal opening 730 can thus provide window for deployment of an infusion catheter branch before reaching the true end of sheath 720. Because distal opening 730 confers a break in the stress that would occur during application of torque or imposed bending by vessel anatomy on sheath 720, the remaining material circumferentially adjacent to distal opening 730 bears the added stress. To reduce the kinking or luminal collapse that could occur within the elevated stress zone, the section of sheath 720 adjacent to distal opening 730 can be constructed of a stiff material. In some cases, this material includes Pebax®, nylon, polytetrafluoroethylene (PTFE) or the like, having a higher durometer as compared to the material used to construct other portions of sheath 720.

Delivery sheath 720 can include detectable markers adjacent to distal opening 730. Here, delivery sheath 720 includes a first detectable marker 750a disposed on the side of sheath 720 opposite to distal opening 730, and a second detectable marker 750b disposed proximal to distal opening 730. Detectable markers 750a, 750b may include, for example, a radiopaque agent such as barium, tungsten, gold, platinum, iridium, palladium, rhodium, and the like. During a surgical or diagnostic procedure, detectable markers such as these can assist a clinician in identifying the position of the tip of sheath 720, and the orientation of distal opening 730 relative to the surrounding patient anatomy and the center of sheath 720. In an exemplary embodiment, one rectangular marker is located at the proximal base of the distal opening with the long edge of the marker oriented parallel to the longitudinal axis of the sheath, and a second marker of the same shape and orientation is positioned on the side of the sheath opposing the distal opening, with the distal edge of the second marker lined up with the distal end of the sheath.

Figure 8A:
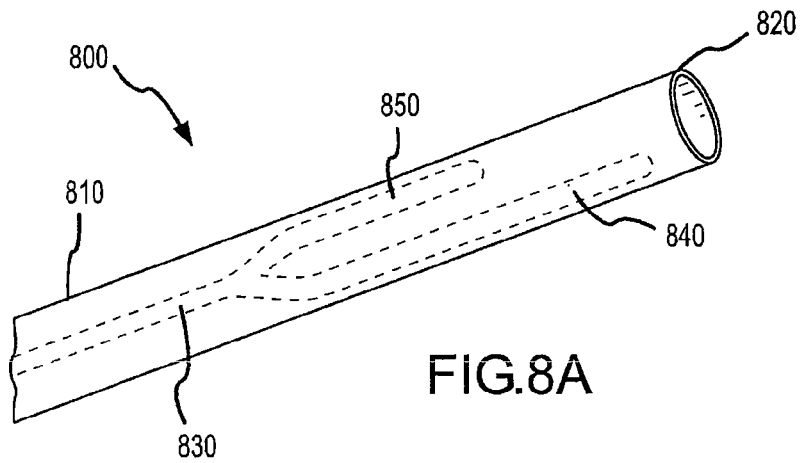
FIGS. 8A, 8B, and 8C show a renal infusion system according to embodiments of the present invention.
Figure 8B:
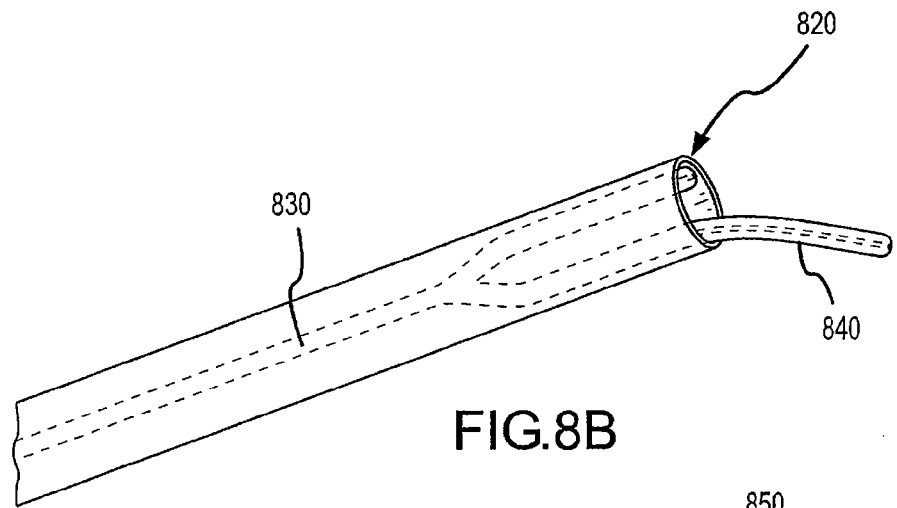
Figure 8C:
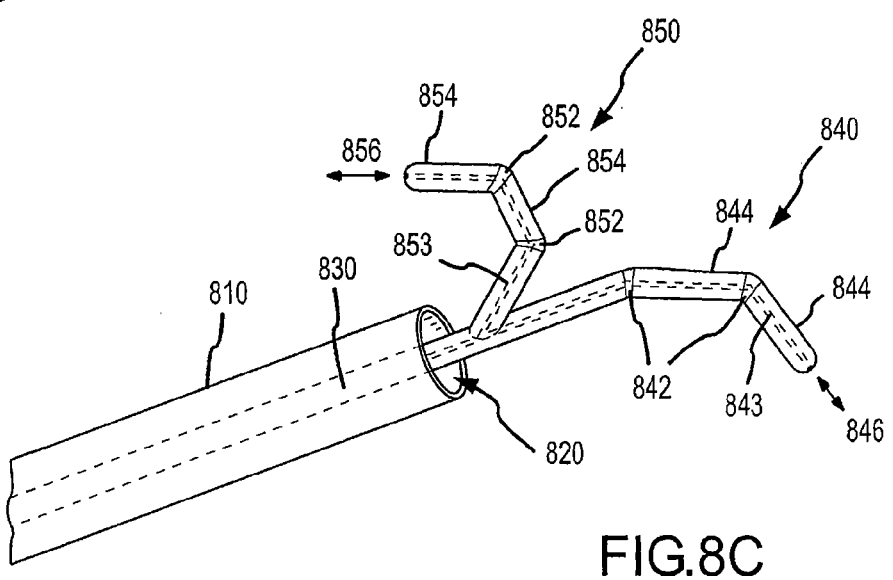

Selective renal cannulation can also be achieved by other embodiments provided herein. For example, as shown in FIGS. 8A and 8B, a renal infusion system 800 may include a delivery sheath 810 having a standard tubular distal end 820, and an offset or asymmetric bifurcated infusion catheter 830. FIG. 8A depicts a bifurcated infusion catheter 830 that includes offset first 840 and second 850 infusion branches, where first infusion branch 840 is longer than second infusion branch 850. Infusion catheter 830 is in a constrained or otherwise undeployed configuration, disposed within an interior lumen of delivery sheath 810. FIG. 8B depicts infusion catheter 830 in a partially unconstrained or otherwise partially deployed configuration, where first infusion branch 840 is advanced distally through tubular distal end 820, while second infusion branch 850 remains constrained or undeployed within delivery sheath 830. In this configuration, infusion catheter 830 is well suited for infusing a distal renal artery of a patient having offset proximal and distal renal arteries, a renal artery of a patient having only one renal artery, or a single renal artery of a patient having two renal arteries. FIG. 8C shows infusion catheter 830 in a fully unconstrained or otherwise deployed configuration, where both first infusion branch 840 and second infusion branch 850 are advanced distally through tubular distal end 820. In this configuration, infusion catheter 830 is well suited for infusing a proximal renal artery and a distal renal artery of a patient having offset proximal and distal renal arteries. For example, lateral deployment of first infusion catheter branch 840 can open an infusion valve and permit infusion into a distal renal artery, and lateral deployment of second infusion catheter branch 850 can open a second infusion valve and permit infusion into a proximal renal artery. Thus, first branch lumen 843 can define an open first flow path 846 that allows infusion or delivery to a distal renal artery, and second branch lumen 853 can define an open second flow path 856 that allows infusion or delivery to a proximal renal artery. In this way, a bifurcated infusion catheter can be advanced to asynchronously deploy both branches and achieve bilateral renal artery cannulation in a patient having offset renal arteries.

In some embodiments, first infusion branch 840 can include bends 842 and segments 844, and second infusion branch 850 can include bends 852 and segments 854. The degree of bilateral renal artery offset in the patient being treated, or the degree of offset that is being targeted in the design of infusion catheter, may be facilitated by branches of different lengths. As such, the spacing of bends 842, 852 and the lengths of segments 844,854 can be designed so as to provide various degrees of lateral offset between first infusion branch 840 and second infusion branch 850 when deployed. In some cases, the bend and segment configurations can be selected so as provide an optimal configuration for a particular patient or group of patients. In some cases, the bends 842 are offset or spaced differently from bends 852, such that the overall flexion of first infusion branch 840 is offset or otherwise asymmetric to the overall flexion of second infusion branch 850. In some cases, the offset distances of the branch bends is equivalent to that of the renal arteries. In some cases, radiopaque markers can be placed at or incorporated into elements of the infusion catheter. For example, such markers can be placed at the bends of the branches and can help the physician operator in distinguishing the branches from each other under fluoroscopy imaging. Systems incorporating such variations of the bifurcated infusion catheter can be used with standard delivery sheaths as well as delivery sheaths having novel window configurations as discussed herein.

Figure 9:
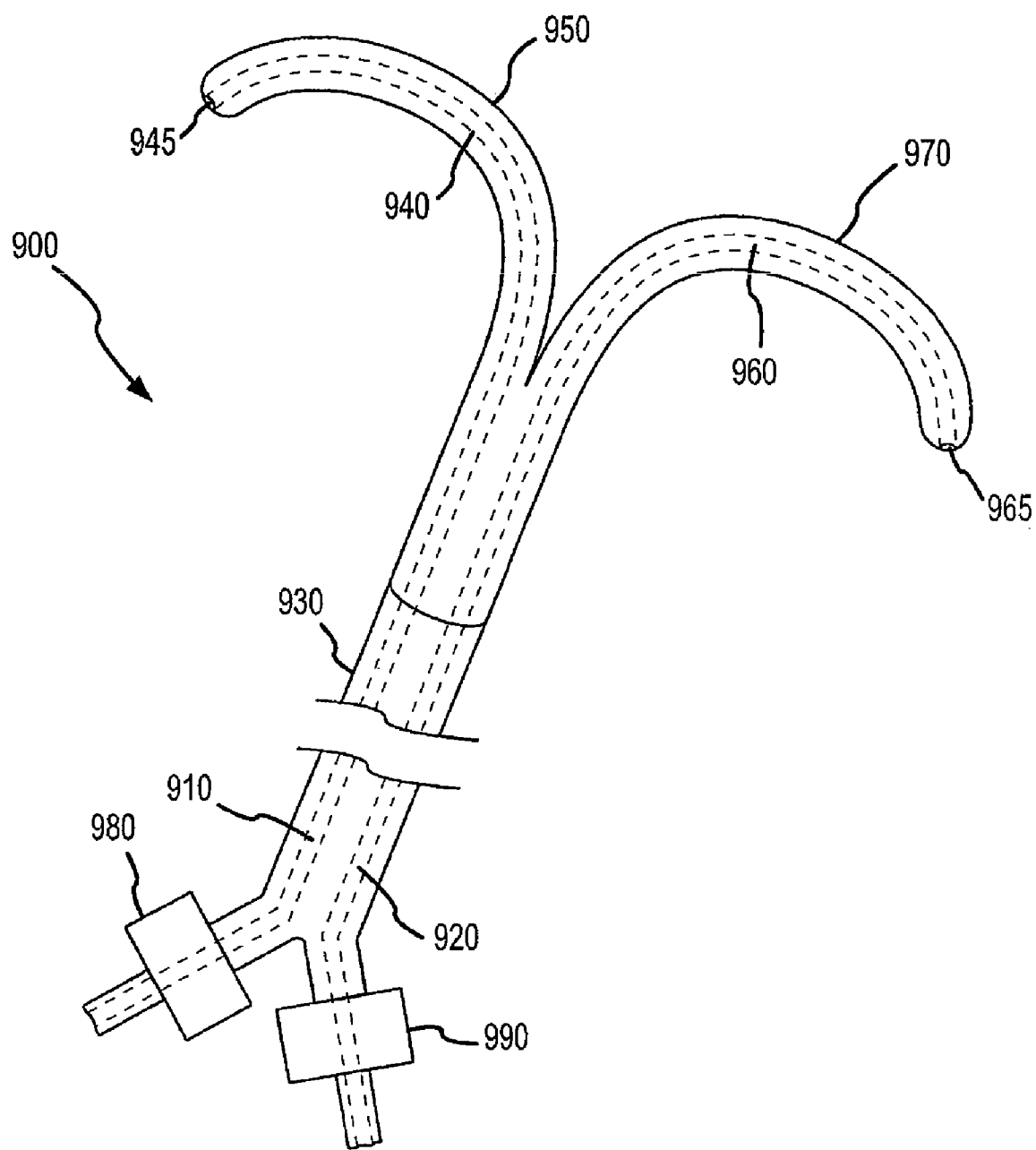
FIG. 9 shows a renal infusion system according to embodiments of the present invention.

In some embodiments, an infusion catheter may include a main body lumen in the body or central shaft of the catheter. The main lumen can be in fluid communication with a first branch lumen disposed within a first branch, and a second branch lumen disposed within a second branch. In some embodiments, such as the one shown in FIG. 9, an infusion catheter 900 may include two independent body lumens 910, 920 in the body or central shaft 930 of the catheter. A first body lumen 910 can be in fluid communication with a first branch lumen 940 disposed within a first branch 950, and a second body lumen 920 can be in fluid communication with a second branch lumen 960 disposed within a second branch 970.

Infusion catheter 900 may also include proximal valve means 980, 990 for regulating flow between an infusion line or source (not shown) and infusion ports 945, 965, respectively. Infusion ports 945, 965 can be disposed at or near the distal tips of branches 950, 970, respectively. In some embodiments, each of valve means 980, 990 may include a two-way stopcock valve so as to allow for independent manual control of the infusion process. Valve means may also be controlled via electronic means, according to desired treatment protocols or programs. In some embodiments, valve means 980, 990 may include pressure regulated valves. Such pressure regulated valves can be configured to remain closed to fluid passage therethrough when the pressure of the distal side of the valve is above aortic blood pressure.

In some embodiments, during retrograde delivery, pressure sensing can be achieved proximally by means of a static fluid column within a fluid lumen of the bifurcated infusion catheter. The static column is distal of the valve, and can transmit pressure from the distal port toward the proximal valve. During delivery of the catheter and prior to cannulation, no infusion through the catheter infusion lumen is occurring. Because valves 980, 990 are closed, pressure that is present at the infusion ports can be sensed by pressure sensors located toward the proximal hub. It is possible to can observe or sense the dynamic pressure head in addition to the aortic blood pressure or stagnation aortic blood pressure, thus keeping the pressure regulated valves 980, 990 closed. In this way, it is possible to sense active aortic flow that encounters the distal end of the static column, at the port (e.g. the stagnation pressure). When a branch cannulates a renal artery and infusion begins, the static column is lost and does not transmit pressure. The distal port of the branch is oriented along the direction of the renal artery flow. The infusion valve no longer observes the stagnation aortic blood pressure and the pressure observed on the distal side of the proximal valve (e.g. valve 980 or 990) falls below that of the aortic blood pressure. Renal artery pressure is less than stagnation aortic blood pressure.

The valve is opened and infusion occurs through the connecting branch port 945, 965. In some embodiments, these features can serve to minimize systemic effects of a drug being administered in an infusion fluid.

Figure 10:
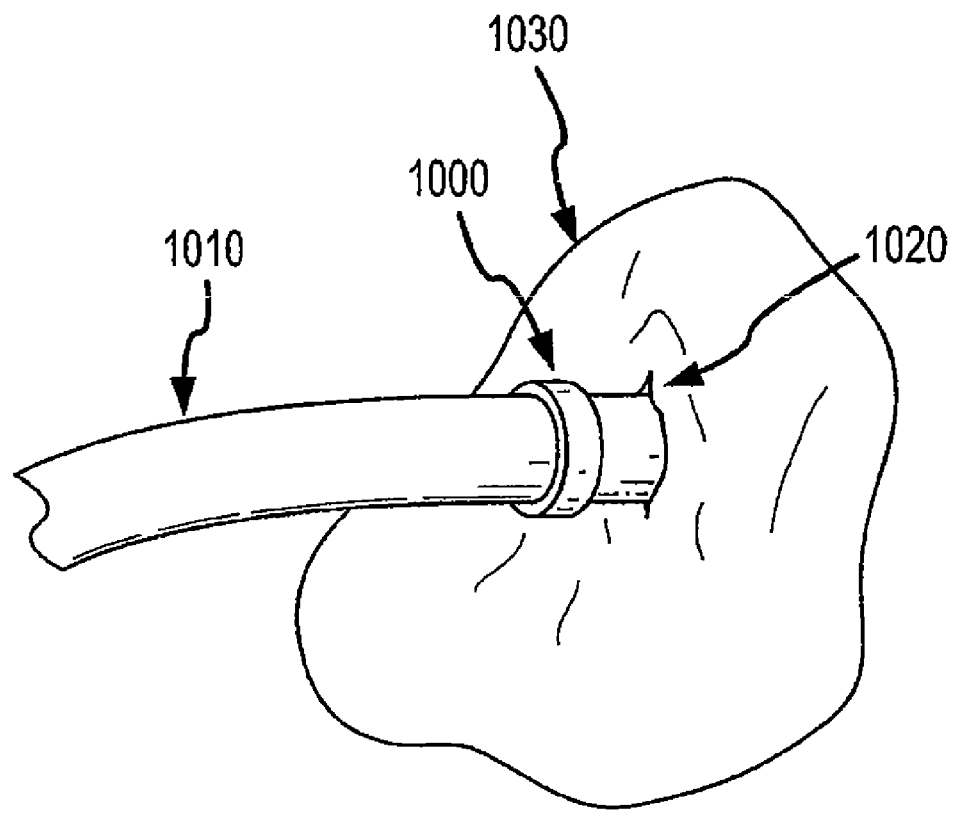
FIG. 10 shows a fastener according to embodiments of the present invention.

In certain clinical circumstances, it is desirable to hold a delivery sheath at a fixed position in the patient during an in-dwell procedure. Often, such procedures can be lengthy in duration. FIG. 10 illustrates a fastening embodiment for preventing accidental or unintended displacement of a delivery sheath during a surgical procedure. Fastener or clip 1000 can secure delivery sheath 1010 in a fixed position relative to a vessel access site 1020, a skin boundary 1030 of a patient, or any other desired reference. In some embodiments, such fasteners or attachment means can be useful in cases involving the targeted delivery of drugs or therapeutic agents to, or the monitoring of biological markers within specific sites within, the vascular anatomy for prolonged durations. A fastener 1000 may also be used to indicate the position or orientation of delivery sheath 1010, a delivery sheath tip, or an infusion catheter, relative to vessel access site 1020 or any other suitable reference. A fastener 1000 can also be used to affix the position and orientation of a delivery sheath 1010.

Once the tip of delivery sheath 1010 is placed, for example, at a desired target vessel site, a physician operator can place clip 1000 externally in contact with the patient's skin 1030. Clip 1000 can be affixed with sheath 1010 via any suitable means. If sheath 1010 becomes proximally displaced during the surgical procedure, the attending staff can be alerted that the sheath tip has moved from its original or intended position by observing the shift in position of clip 1000. Conversely, distal displacement of sheath 1010 is prevented or inhibited due to the abutment of clip 1000 against the patient's skin 1030.

Figure 11:
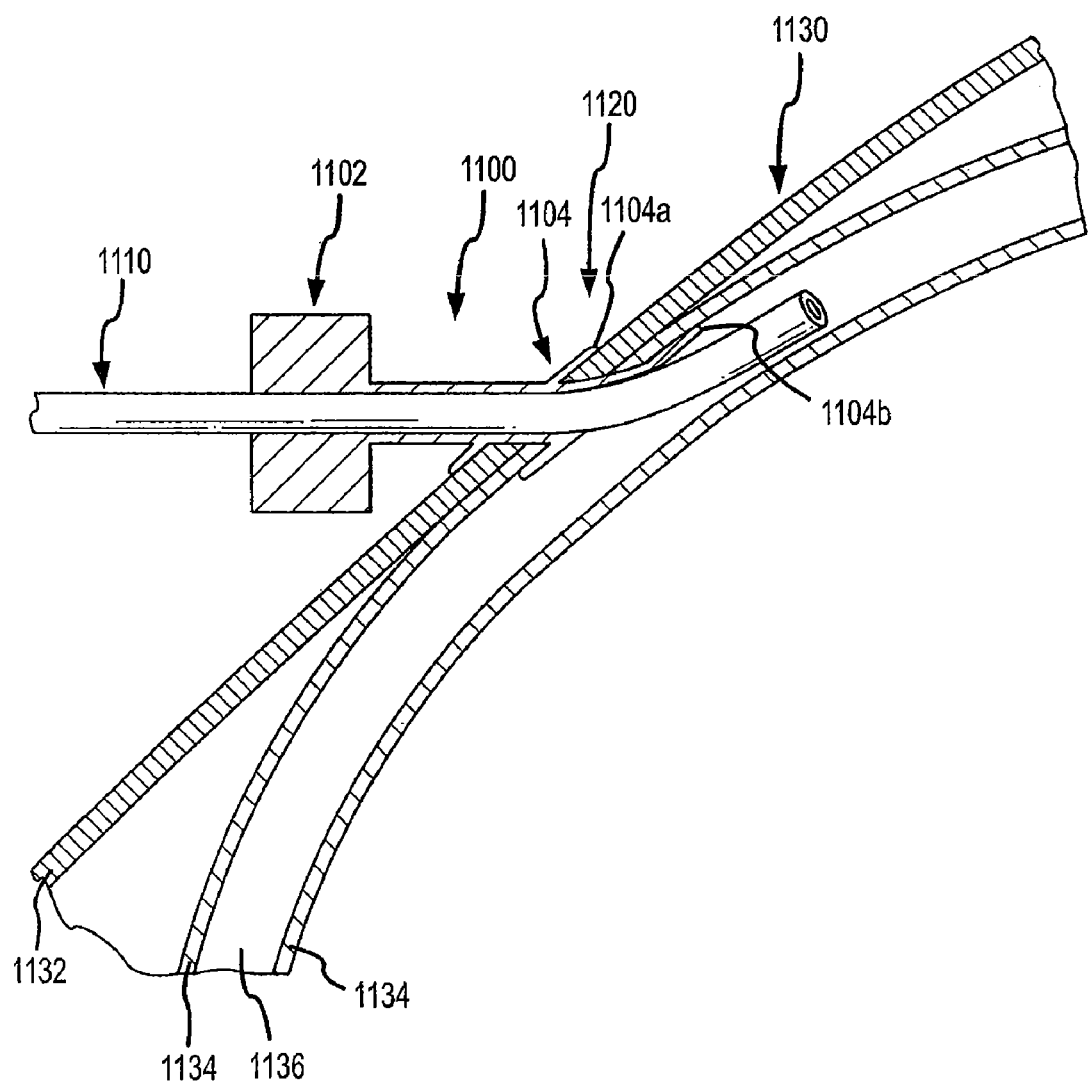
FIG. 11 shows a fastener according to embodiments of the present invention.

FIG. 11 illustrates another fastening embodiment for preventing accidental or unintended displacement of a delivery sheath during a surgical procedure. Fastener or clip 1100 can secure delivery sheath 1110 in a fixed position relative to a vessel access site 1120, a skin boundary 1130 of a patient, or any other desired reference. In some embodiments, such fasteners can be useful in cases involving the targeted delivery of drugs or therapeutic agents to, or the monitoring of biological markers within specific sites within, the vascular anatomy for prolonged durations. A fastener 1100 may also be used to indicate the position or orientation of delivery sheath 1110, a delivery sheath tip, or an infusion catheter, relative to vessel access site 1120 or any other suitable reference. A fastener 1100 can also be used to affix the position and orientation of a delivery sheath 1110. Fastener 1100 includes a locking component 1102 that fixes fastener 1100 relative to sheath 1110. Fastener 1100 also includes a pincher component 1104 having an external flange 1104a and an internal flange 1104b. In use, external flange 1104a and internal flange 1104b can operate to pinch skin tissue 1132 and an artery wall 1134 together. The external flange may include adhesive. The combination of locking component 1102 and pincher component 1104 can prevent or inhibit both translational (i.e. proximal or distal) or rotational displacements of delivery sheath 1110 relative to its original or intended position or conformation within vessel lumen 1136.

Figure 12:
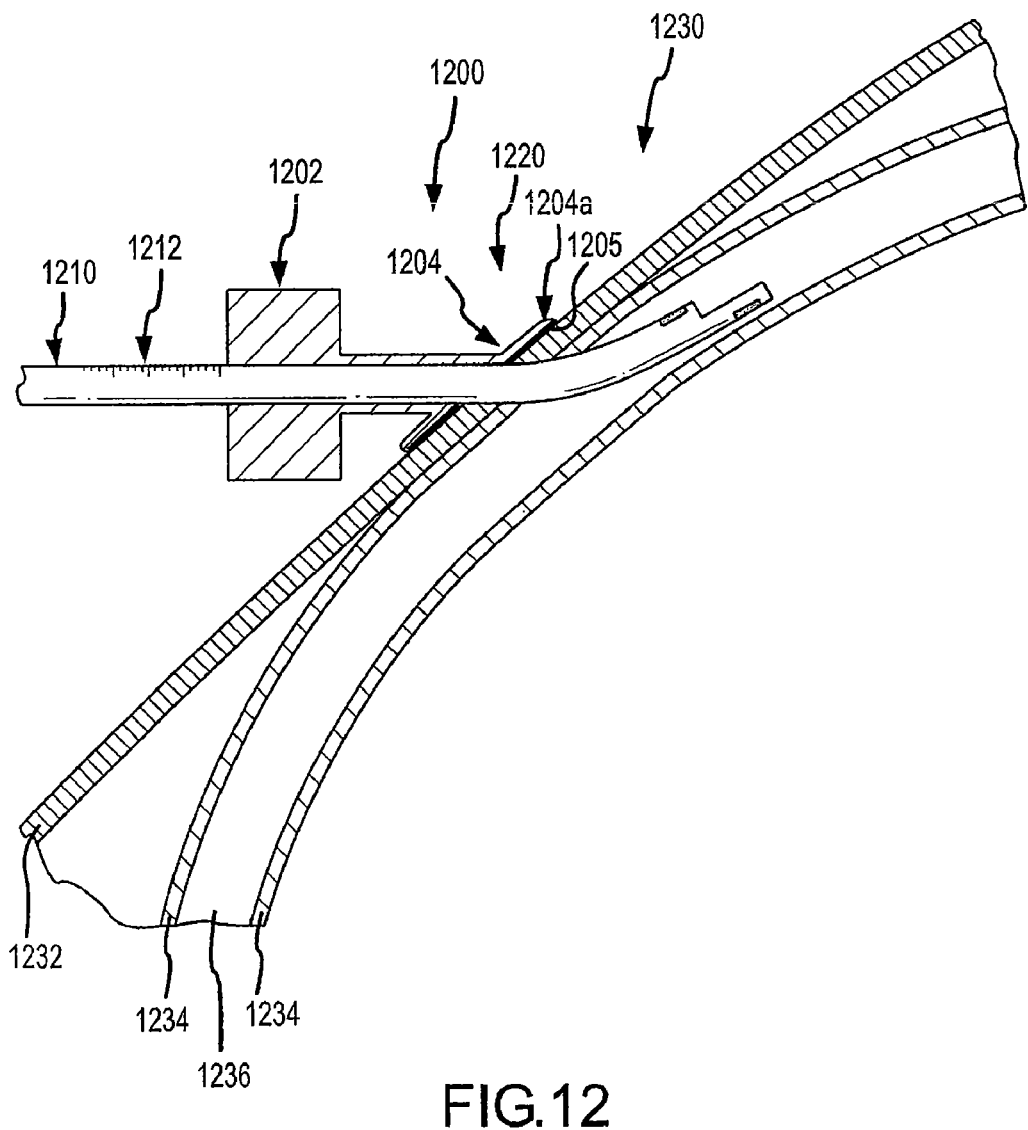
FIG. 12 shows a fastener according to embodiments of the present invention.

FIG. 12 illustrates another fastening embodiment for preventing accidental or unintended displacement of a delivery sheath during a surgical procedure. Fastener or clip 1200 can secure delivery sheath 1210 in a fixed position relative to a vessel access site 1220, a skin boundary 1230 of a patient, or any other desired reference. In some embodiments, such fasteners can be useful in cases involving the targeted delivery of drugs or therapeutic agents to, or the monitoring of biological markers within specific sites within, the vascular anatomy for prolonged durations. A fastener 1200 may also be used to indicate the position or orientation of delivery sheath 1210, a delivery sheath tip, or an infusion catheter, relative to vessel access site 1220 or any other suitable reference. A fastener 1200 can also be used to affix the position and orientation of a delivery sheath 1210. Fastener 1200 includes a locking component 1202 that fixes fastener 1200 relative to sheath 1210. Fastener 1200 also includes an adhesive component 1204 having an external flange 1204a. In some embodiments, external flange 1204a can include an adhesive material 1205 that fixes external flange 1204a with the external surface of patient skin 1232. In some embodiments, a separate adhesive member or substance can be inserted between or applied to the interface between external flange 1204a and patient skin 1232, in place of or in addition to adhesive material 1205 of external flange 1204a. For example, a circular double-sided adhesive pad, extending radially about delivery sheath 1210, can be inserted between external flange 1204a and patient skin 1232. In use, such a pad can help prevent or inhibit movement of delivery sheath 1210 relative to a desired position within vessel lumen 1236. In some embodiments, delivery sheath 1210 includes coded markings 1212 that indicate the distance between an axial position on the sheath and its distal tip. Such markings may be useful for a physician operator, for example, in clinical circumstances where the physician wishes to adjust the position of the sheath tip from a first position to a second position (e.g. within a limited displacement range) and later bring the sheath tip back to its first position. This may be done with or without the concomitant use of fluoroscopy.

The pincher means and adhesive means described herein can help ensure hemostasis between the delivery sheath and the patient skin within the vessel access site. The functional synergy of the locking means and the pincher or adhesive means can prevent or inhibit rotational or translational displacement of the delivery sheath from the original or intended position or orientation.

While the above provides a full and complete disclosure of certain embodiments of the present invention, various modifications, alternate constructions and equivalents may be employed as desired. Therefore, the above description and illustrations should not be construed as limiting the invention, which is defined by the appended claims.

What is claimed is:

1. A renal infusion system, comprising:
   an infusion catheter having a bifurcated distal end with a first branch and second branch, said branches being biased to deploy laterally when unconstrained; and
   a delivery sheath having a lumen which receives the infusion catheter and constrains the first branch and second branch;
   wherein one of the first and second branches opens laterally through a distal opening of the delivery sheath while the other of the first and second branches remains fully constrained within the delivery sheath, and
   wherein the first branch comprises a first branch lumen and a first branch infusion port, and the second branch comprises a second branch lumen and a second branch infusion port.

2. A renal infusion system as in claim 1, wherein the distal opening comprises an elongate structure on one side of the sheath and is free from a constraining structure on the other side of the sheath.

3. A renal infusion system as in claim 1, wherein the distal opening is chamfered.

4. A renal infusion system as in claim 1, wherein the distal opening has an axial deployment window opposite to a solid wall.

5. A renal infusion system as in claim 4, wherein the delivery sheath has a lateral protrusion proximal and diametrically opposite to the axial deployment window, wherein the protrusion can balance a force caused by deployment of a single branch of the infusion catheter.

6. A renal infusion system as in claim 1, wherein the delivery sheath comprises a detectable marker disposed adjacent the distal opening.

7. A renal infusion system as in claim 1, wherein the delivery sheath comprises a first detectable marker disposed proximally adjacent to the distal opening and a second detectable marker disposed laterally adjacent to the distal opening.

8. A renal infusion system as in claim 7, wherein the first detectable marker is disposed on a first side of the sheath and the second detectable marker is disposed on a second side of the sheath that is opposite to the first side.

9. A renal infusion system as in claim 1, wherein the delivery sheath comprises a semi circular curve disposed proximal to the distal opening, such that an arc of the semi circular curve projects in a first direction, and the distal opening faces a second direction opposite to the first direction.

10. A renal infusion system as in claim 1, further comprising an attachment means configured to secure the delivery sheath with a vessel access site of a patient.

11. An infusion catheter, comprising:
a catheter body having a distal end with a first branch, said branch being biased to deploy laterally when unconstrained; and
a first valve structure disposed between a main lumen in the catheter body and a branch lumen in the first branch, wherein said first valve structure is closed when the first branch is undeployed and opens in response to lateral deployment of the first branch.

12. An infusion catheter as in claim 11, wherein the distal end is bifurcated and further comprises a second branch that is biased to deploy laterally when unconstrained, the infusion catheter further comprising a second valve structure disposed between the main lumen and a branch lumen in the second branch, wherein said second valve structure is closed when the second branch is undeployed and opens in response to lateral deployment of the second branch.

13. An infusion catheter as in claim 12, wherein the first branch is longer than the second branch.

14. An infusion catheter as in claim 11, wherein the first valve comprises a two-way valve.

15. An infusion catheter as in claim 11, wherein the first valve comprises a pressure regulated valve that remains closed when a distal side fluid pressure is greater than an aortic blood pressure of the patient.

16. A renal infusion system, comprising:
a delivery sheath configured for placement within an aorta of a patient;
a first catheter branch configured for advancement through the delivery sheath toward a first renal artery of the patient;
a first flow path that passes through the first catheter branch to provide a first fluid flow toward the first renal artery;
a first valve that regulates the first flow path when the first branch is in a constrained and released configuration;
a second catheter branch configured for advancement through the delivery sheath toward a second renal artery of the patient;
a second flow path that passes through the second catheter branch to provide a second fluid flow toward the second renal artery; and
a second valve that regulates the second flow path when the second branch is in a constrained and released configuration; and
wherein the first fluid flow through the first flow path is greater when the first branch is in the released configuration than when it is in the constrained configuration.

17. The system of claim 16, wherein the delivery sheath comprises a marker.

18. The system of claim 16, wherein the first branch is in the constrained configuration when disposed within the delivery sheath, and is in the released configuration when advanced through a deployment window of the delivery sheath.

19. The system of claim 16, wherein the first valve comprises a first notch valve that constricts the first flow path when the first branch is in the constrained configuration, and that dilates the first flow path when the first branch is in the released configuration.

20. The system of claim 16, wherein the delivery sheath comprises a semi circular curve disposed proximal to the deployment window, such that an arc of the semi circular curve projects in a first direction, and the deployment window faces a second direction opposite to the first direction.

21. The system of claim 16, wherein the first branch comprises a marker.

22. The system of claim 16, wherein the first valve comprises a two-way valve.

23. The system of claim 16, wherein the first valve comprises a pressure regulated valve that remains closed when a distal side fluid pressure is greater than an aortic blood pressure of the patient.

24. The system of claim 16, further comprising an attachment means configured to secure the delivery sheath with a vessel access site of the patient.

25. The system of claim 16, wherein the first catheter branch is longer than the second catheter branch.

* * * * *